(12) United States Patent
Bushek et al.

(10) Patent No.: US 6,325,755 B1
(45) Date of Patent: Dec. 4, 2001

(54) MOUNTABLE TRANSDUCER ASSEMBLY WITH REMOVABLE SLEEVE

(75) Inventors: Donald J. Bushek, Plymouth; Clair Madsen, Maple Grove, both of MN (US); Iain Grant, Columbus, OH (US)

(73) Assignee: St. Croix Medical, Inc., Minneapolis, MN (US)

( * ) Notice: Subject to any disclaimer, the term of this patent is extended or adjusted under 35 U.S.C. 154(b) by 0 days.

(21) Appl. No.: 09/245,231

(22) Filed: Feb. 5, 1999

Related U.S. Application Data

(63) Continuation-in-part of application No. 08/908,233, filed on Aug. 7, 1997, now Pat. No. 6,001,129.

(51) Int. Cl.[7] .................................................. H04R 25/00
(52) U.S. Cl. ................................ 600/25; 623/10; 606/130
(58) Field of Search .......................... 600/25; 607/55–57; 606/60–61, 130; 623/10–11, 16

(56) References Cited

U.S. PATENT DOCUMENTS

| 4,957,507 | 9/1990 | Lenkauskas . |
| 5,993,376 | * 11/1999 | Kennedy ................................ 600/25 |
| 6,001,129 | * 12/1999 | Bushek et al. ......................... 600/25 |

FOREIGN PATENT DOCUMENTS

| 0 231 162 A1 | 8/1987 | (EP) . |
| WO 98/06235 | 2/1998 | (WO) . |
| WO 98/06237 | 2/1998 | (WO) . |

* cited by examiner

*Primary Examiner*—John P. Lacyk
(74) *Attorney, Agent, or Firm*—Fredrikson & Byron, P.A.

(57) ABSTRACT

A mountable transducer assembly with removable sleeve provides for efficient and versatile implantation of transducers that are part of an implantable hearing assistance system. The invention provides for a universal connector and bracket where the universal connector can be removed from the bracket without the necessity of unmounting the bracket from its implanted location, for example, attached to the mastoid bone in the middle ear region. Further, the invention provides for three-dimensional movement of a transducer assembly attached to a removable column which further extends the flexibility and options for an implantation surgeon when implanting an implantable hearing-assistance device requiring one or more transducers. The sleeve, with attached transducer assembly, is further slidably adjustable in a longitudinal manner, to further extend the options and flexibility for the implantation surgeon to achieve good contact between a transducer and a target anatomical structure within the middle ear. There are further options for the implantation surgeon to use non-functioning replicas of the transducer assembly that can be both pliable and transparent to further aid in sizing the transducer and transducer assembly for successful implantation within a hearing-impaired subject.

37 Claims, 20 Drawing Sheets

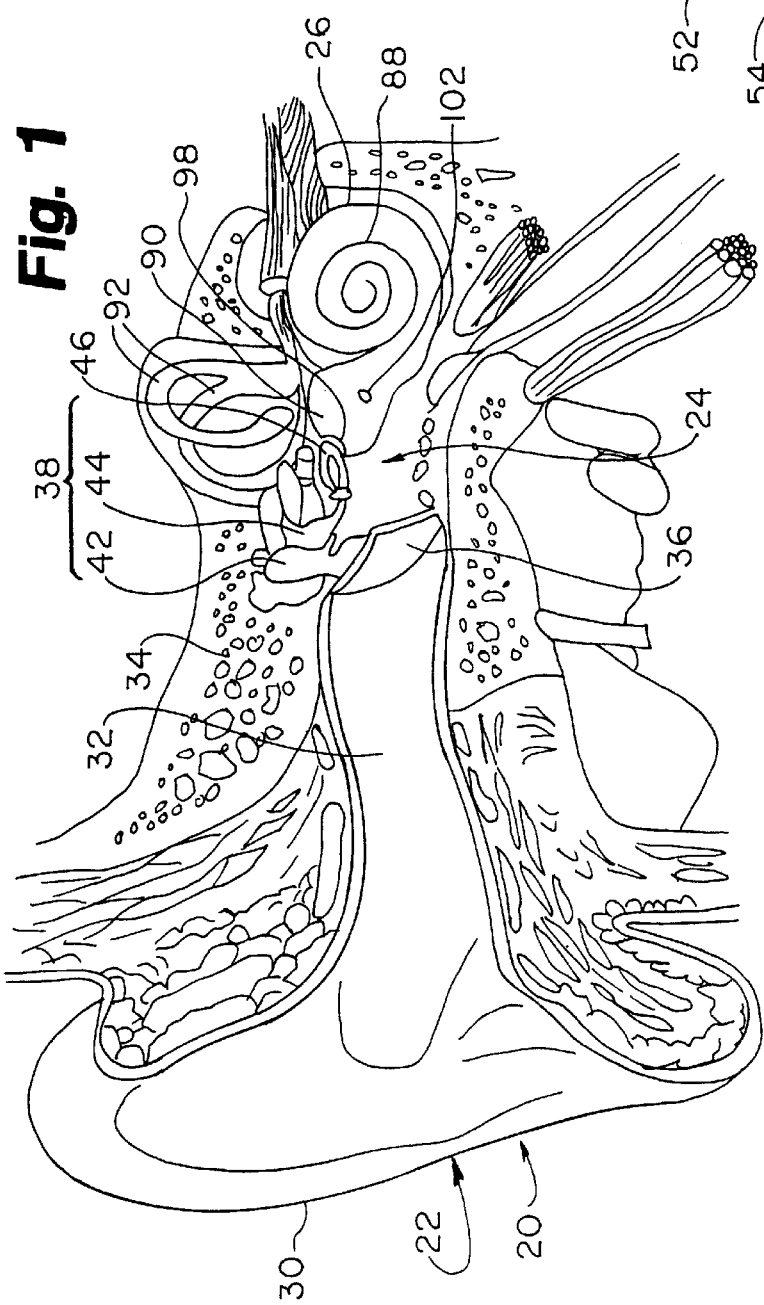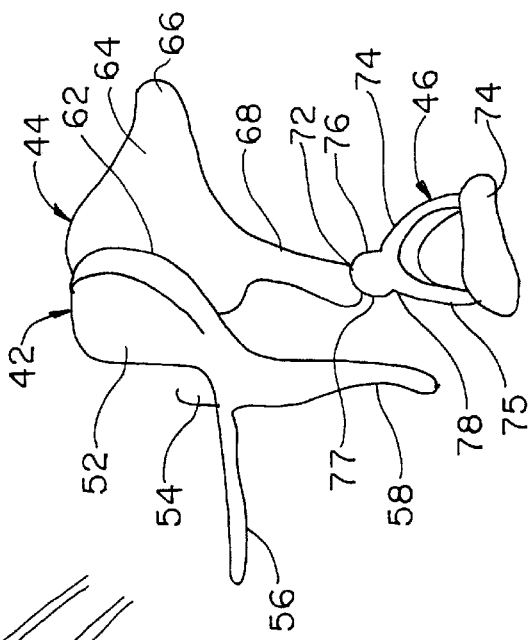

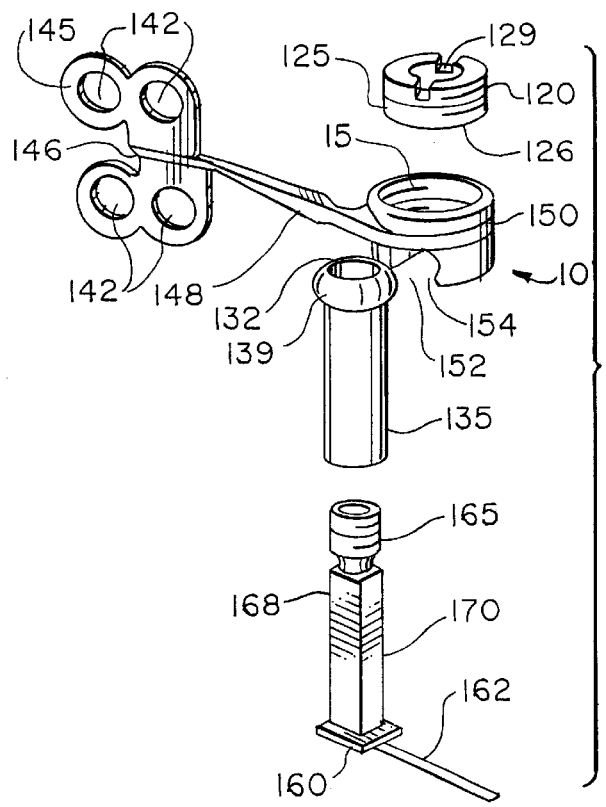
Fig. 3
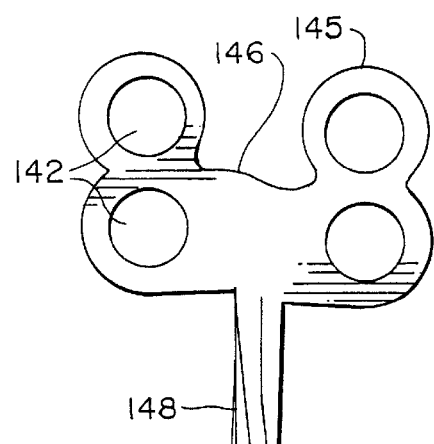
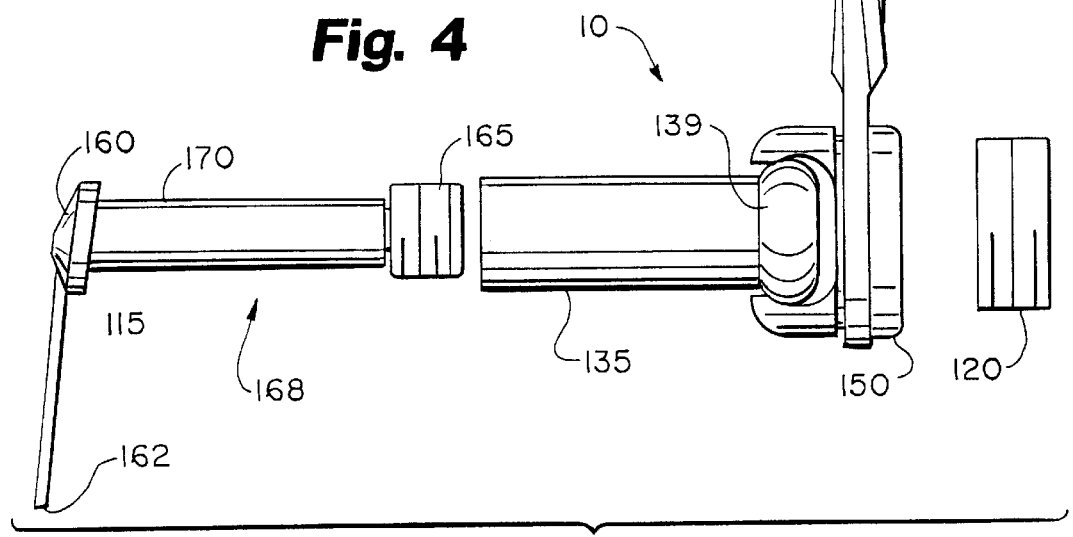
Fig. 4

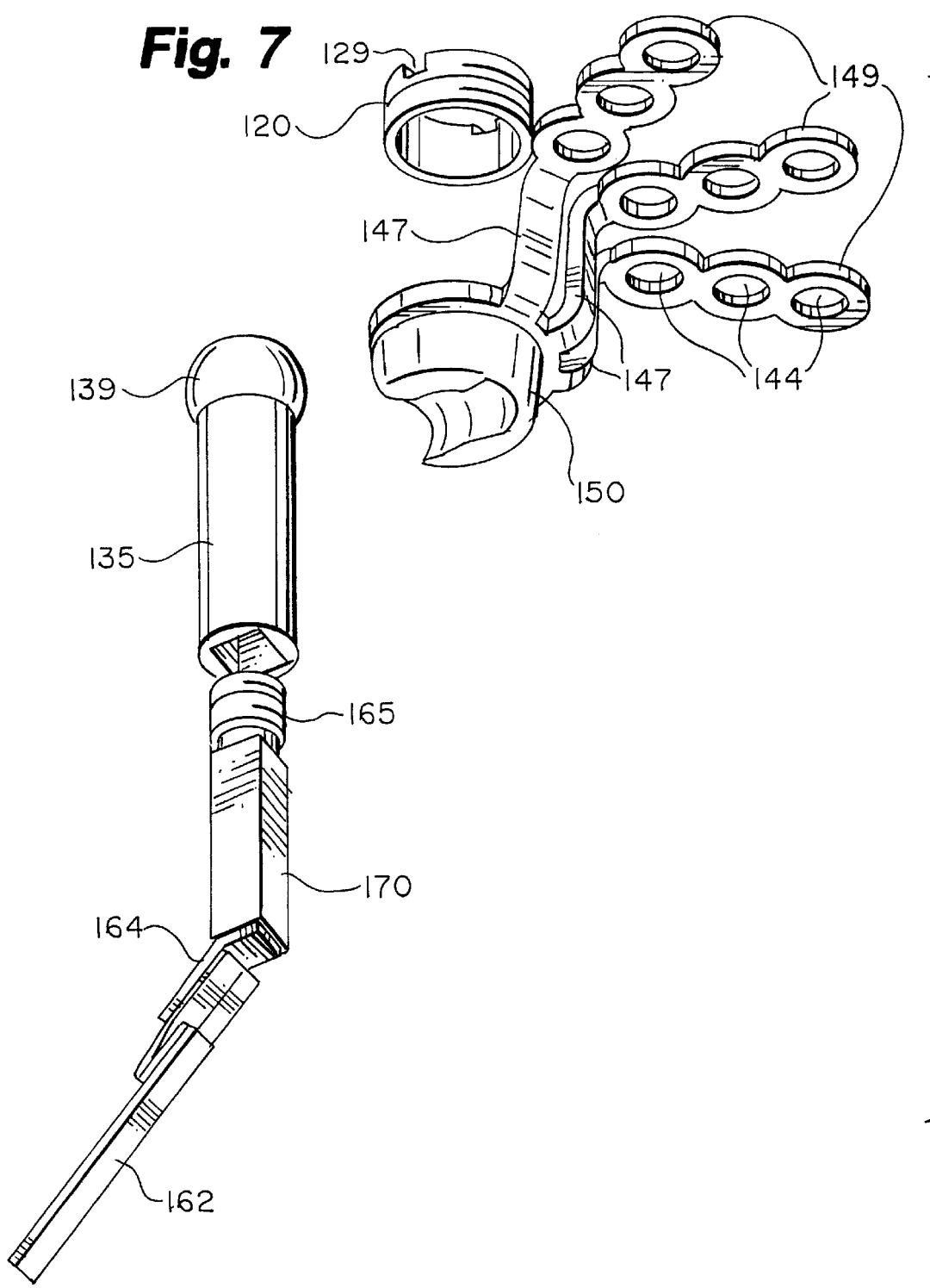

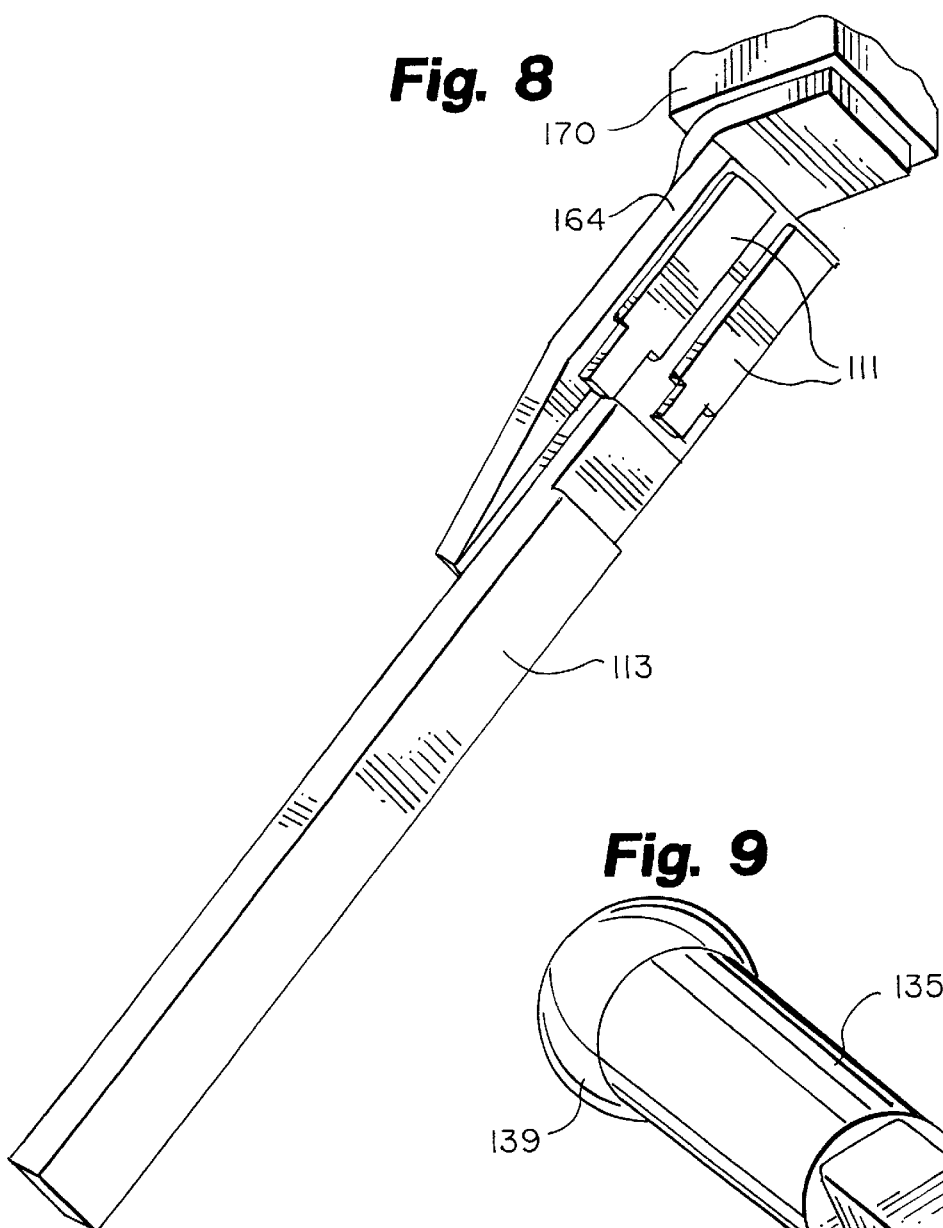
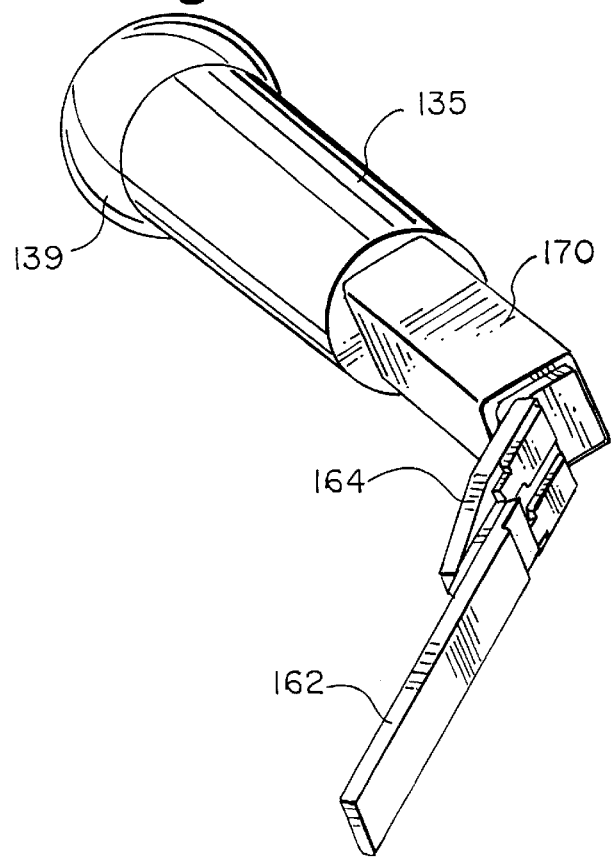

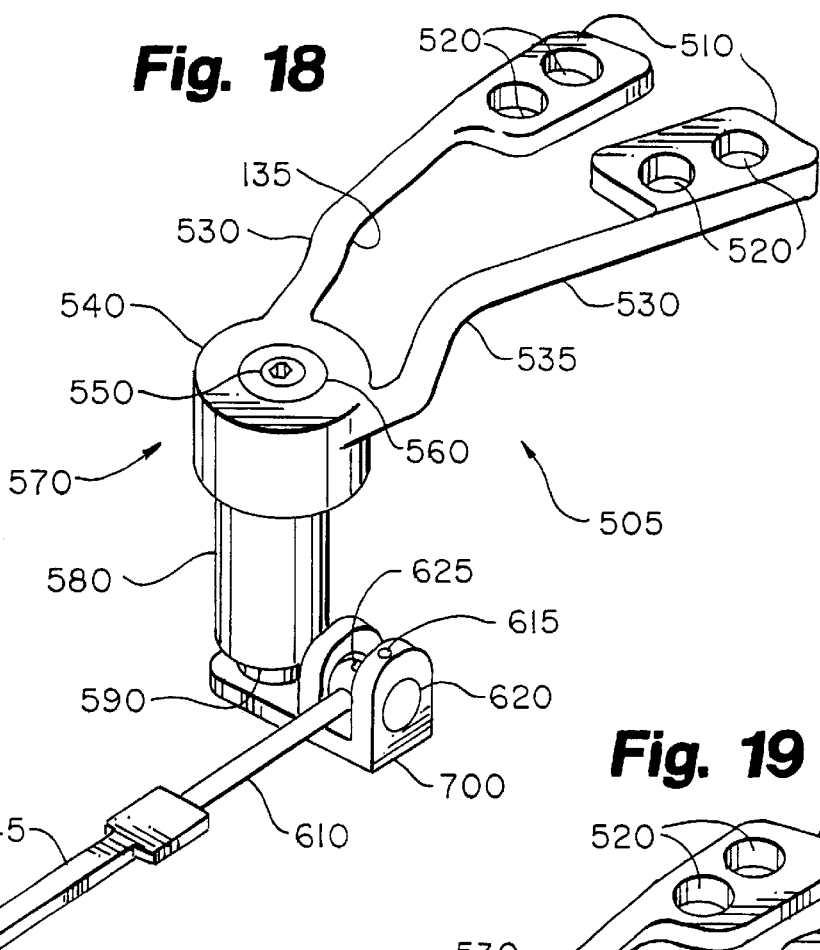
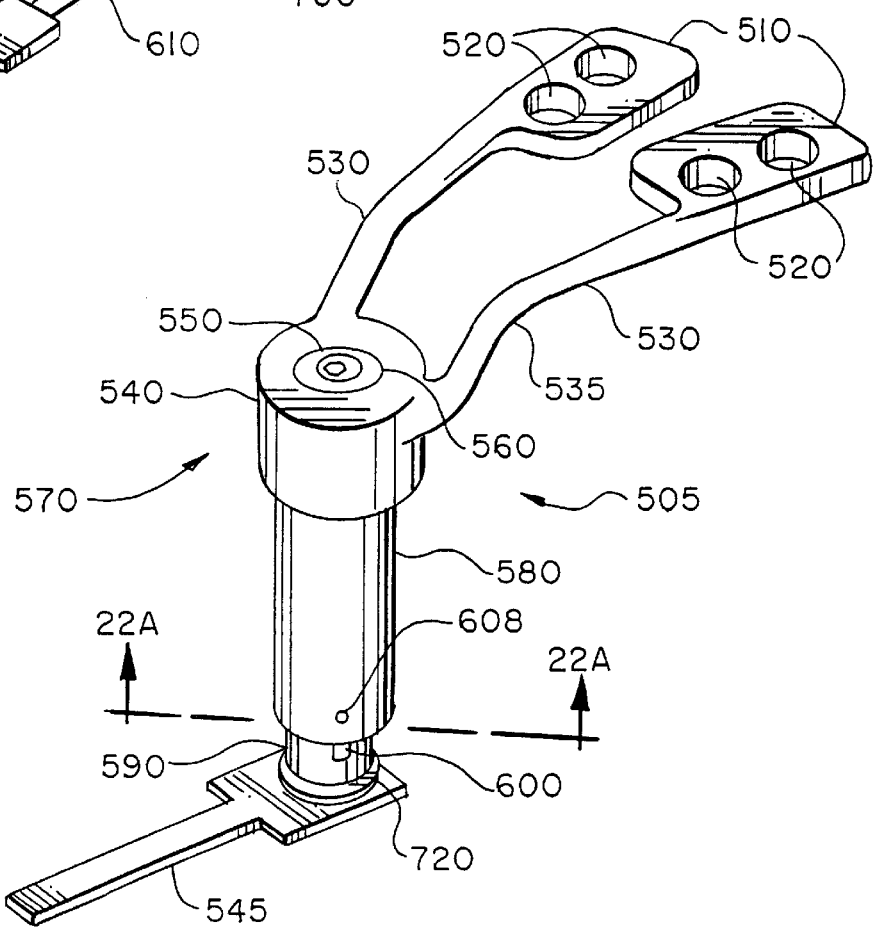

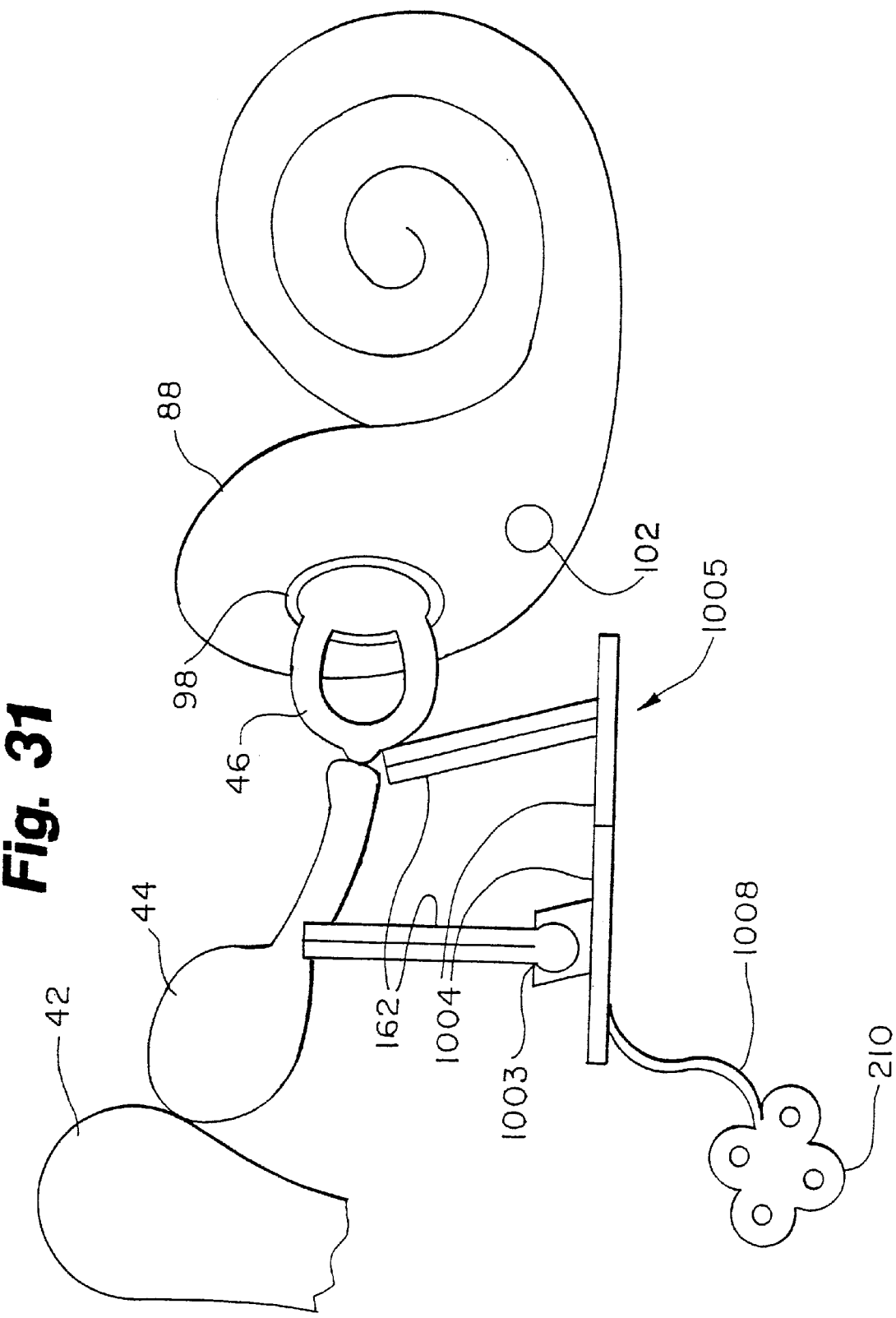

MOUNTABLE TRANSDUCER ASSEMBLY WITH REMOVABLE SLEEVE

CROSS-REFERENCE TO RELATED APPLICATION

This is a Continuation-in-Part application and is directed to subject matter that is related to the subject matter of commonly assigned U.S. application Ser. No. 08/908,233, filed Aug. 7, 1997, now U.S. Pat. No. 6,001,129 which is incorporated herein by reference.

BACKGROUND OF THE INVENTION

1. Field of the Invention

This invention relates to mounting implantable transducers for use in a hearing aid system within the middle ear.

2. Description of Related Art

In a patient with normally functioning anatomical hearing structures, sound waves are directed into an ear canal by the outer ear and into contact with a tympanic membrane. The tympanic membrane is located at the terminus of the ear canal. The pressure of the sound waves vibrates the tympanic membrane resulting in the conversion to mechanical energy. This mechanical energy is communicated through the middle ear to the inner ear by a series of bones located in the middle ear region. These bones of the middle ear are generally referred to as the ossicular chain, which includes three primary components, the malleus, the incus and the stapes. These three bones must be in functional contact in order for the mechanical energy derived from the vibration of the tympanic membrane to be transferred through the middle ear to the inner ear.

In a patient possessing normal hearing capacity, the tympanic vibrations are mechanically conducted through the malleus, incus, and stapes to the oval window and then into the fluid in the cochlea of the inner ear. Within the cochlea, the mechanical vibrations generate fluidic motion. This fluidic motion is converted into neural impulses and the brain interprets these impulses and derives the patient's perception of sound. A variety of disorders, however, can disrupt or impair normal hearing. These disorders include disorders of the tympanic membrane as well as disorders of the ossicular chain and/or inner ear.

Implantable devices are often useful for assisting with hearing. Such devices include partial middle ear implantable (P-MEI) or total middle ear implantable (T-MEI) devices, cochlear implants, and other hearing assistance systems that use components disposed in the middle or inner ear regions. These components may include an input transducer for receiving sound vibrations or an output stimulator for providing mechanical or electrical output stimuli based on the received sound vibrations.

The cochlear implant, for instance, is an electronic device that allows profoundly deaf people to hear by electrical stimulation of the auditory nerve fibers within the inner ear. Typically, an external microphone will transpond sound waves into electrical energy. A processor will amplify the electrical energy, filter it, and send it to a transmitter which changes the electrical signals into magnetic signals. An implanted receiver transcutaneously senses the magnetic currents, transforms it to an electrical signal, which travels to the cochlea via a wire electrode. This electrode directly stimulates nerve fibers present in the cochlea. The brain perceives this stimulation as sound (see also U.S. Pat. No. 3,764,748).

Some types of partial middle ear implantable (P-MEI), total middle ear implantable (T-MEI), cochlear implant, or other hearing assistance systems utilize components disposed within the middle ear or inner ear regions. Such components may include an input transducer for receiving sound vibrations or an output stimulator for providing mechanical or electrical output stimuli based on the received sound vibrations.

An example of one such device is disclosed in U.S. Pat. No. 4,729,366, issued to D. W. Schaefer on Mar. 8, 1988. In the '366 patent, a mechanical-to-electrical piezoelectric input transducer is associated with a malleus bone in the patient's middle ear. The malleus vibrates in response to sounds received at the patient's tympanic membrane (eardrum). The piezoelectric input transducer transduces a mechanical energy of the malleus vibrations into an electrical signal, which is amplified and further processed by an electronics unit. A resulting electrical signal is provided to an electrical-to-mechanical piezoelectric output transducer that generates a mechanical vibration that is coupled to a stapes bone in the ossicular chain or to an oval window or round window of a cochlea. In the '366 patent, the ossicular chain is interrupted by removal of an incus bone. Removal of the incus prevents the mechanical vibrations delivered by the piezoelectric output transducer from mechanically feeding back to the piezoelectric input transducer.

Piezoelectric transducers are one example of a class of electromechanical transducers that require contact to sense or provide mechanical vibrations. For example, the piezoelectric input transducer in the '366 patent contacts the malleus for detecting mechanical vibrations. In another example, the piezoelectric output transducer in the '366 patent contacts a stapes bone or the oval or round window of the cochlea.

Devices for assisting the hearing impaired patient range from miniaturized electronic hearing devices which can be adapted to be placed entirely within the auditory canal, or implantable devices which can be completely or partially implanted within the skull. For those hearing systems, or portions of hearing systems, that require complete subcranial implantation, a challenge has existed to adapt the implantable device for optimal mounting to the unique patient morphologies (including both naturally occurring as well as those created by surgical processes) among patients. The access site for accessing the implantation area for hearing systems is normally posterior to the flap (or pinna) of the outer ear. The precise morphology of the implantation area of any given patient is normally not determinable until surgical entry into the implantation area is achieved. Thus, it is difficult to fabricate a device that will operably fit within the implantation area prior to surgically accessing the implantation site.

Known implantable devices that have elements which perform a support or mounting function are typically rigidly mounted to a bone within the middle ear region. However, once such systems are positioned and mounted, the devices are not removable from the implantation area without disengaging the support device and any attached apparatus from the bone. As can be readily appreciated removal of previously mounted supporting brackets from tissue and bone creates undesirable trauma as well as stripping of the bone screw holes rendering the holes nearly useless if remounting is necessary.

Further difficulties have arisen with the use of implantable devices in facilitating the fine adjustments necessary to properly position and configure the support assembly and attached transducers so as to contact an auditory element and thus vibrate a portion of the ossicular chain, e.g., the stapes.

Such devices present a particular problem in that positioning, or docking, of the transducer against the auditory element in a stable configuration requires extremely fine adjustments that are difficult given the location of the auditory elements and the attendant lack of maneuvering room.

SUMMARY OF THE INVENTION

To address the difficulties noted above, it is an object of this invention to provide an apparatus and method of use for more efficiently and accurately positioning and mounting an implantable hearing aid system transducer support assembly within a patient's middle ear or adjacent cavity. A transducer is coupled to a mounting support and positioned in the middle ear with an accompanying electronics unit being separately inserted for ease of implantation. Because the transducer support and electronics units are not attached, repair or maintenance of the electronics unit does not necessitate the need to remove or adjust the support.

It is yet another object of this invention to promote a single mounting flange with a plurality of apertures is mounted in the middle ear. The mounting flange is flexible to allow positioning of the apertures substantially flush with the mounting area of the mastoid bone. A flexible neck connects the mounting flange with a hanger portion. The hanger is configured to accept a sleeve with an attached transducer assembly at one end, and the retaining nut at the other end. The hanger is devised so that the sleeve with the attached transducer assembly can be removed and reinserted without removing the mounting flange attached to the mastoid bone. Further, different lengths of the support assembly are interchangeable to address anatomical differences among patients. The sleeve is both rotationally and pivotally coupled with the hanger to allow adjustments to be made within the implantation area while the sleeve is coupled with the hanger. The retaining nut is received into the top of the hanger portion and engages the top of the sleeve. When sufficient pressure is exerted upon the sleeve by the retaining nut, the sleeve is secured in its proper position. The attached transducer assembly can move slidably within the sleeve to either lengthen or shorten the overall length of the sleeve and transducer assembly, further allowing adjustment of the transducer within the implantation area.

Yet another object of this invention is to provide a transducer with a flexible connection to its support member allowing for fine adjustment of the transducer by bending. A further preferred embodiment of the subject invention contemplates multiple, bendable mounting flanges connected to the hanger via multiple flexible necks to increase the number of potential mounting positions and sites within the implantation area.

Another object of this invention is to provide a support comprising a single component mounted at one end to a bone mass within the middle ear region. The support is adjustable at a plurality of locations along its length to facilitate positioning of the support at a suitable position in the middle ear. A transducer is positioned at and extending from a second end of the support. The plurality of adjustment mechanisms enable proper placement of the transducer so as to engage a portion of the ossicular chain.

A further object of this invention is to provide a support comprising a single component mounted at one end to a bone mass within the middle ear region. The support is adjustable at a plurality of locations along its length to facilitate positioning of the support at a suitable position in the middle ear. A sensor is positioned at and extending from a second end of the support. The plurality of adjustment mechanisms further enable proper placement of the sensor so as to engage a portion of a disarticulated ossicular chain, such as the stapes.

Still another object of this invention is to provide a support that is adjustable at a plurality of locations along its length to enable a near full range of motion to the support assembly and to facilitate positioning of the support at a suitable position in the middle ear. A driver is positioned at and extends from a second end of the support. The plurality of adjustment mechanisms enable proper placement of the driver so as to engage a predetermined portion of the ossicular chain, such as the malleus.

The transducers referred to above may be input transducers (sensors or microphones) or output transducers (drivers), depending on the particular embodiment of the invention.

BRIEF DESCRIPTION OF THE DRAWINGS

Embodiments of the invention will be described with reference to the Figures, in which like reference numerals denote like elements and in which:

FIG. 1 illustrates a frontal section of an anatomically normal human right ear in which the invention operates.

FIG. 2 is a more enlarged view of the ossicular chain within the middle ear as shown in FIG. 1.

FIG. 3 depicts one embodiment of the invention with a single mounting flange.

FIG. 4 depicts a side view of one embodiment of the invention with the sleeve engaged in the hanger.

FIG. 7 shows another view of the embodiment depicted in FIG. 6.

FIG. 8 is an enlarged view of a portion of the structures shown in FIG. 7, showing the construction of the transducer and the electrical contacts.

FIG. 9 shows yet another view of a portion of FIG. 7 wherein the sleeve and the transducer assembly are shown engaged with one another.

FIG. 18 is a perspective view of a further embodiment of the present invention.

FIG. 19 is a perspective view of still another embodiment of the present invention.

FIG. 31 shows another embodiment of the present invention configured with dual transducers.

DETAILED DESCRIPTION OF PREFERRED EMBODIMENTS

Figure 5:
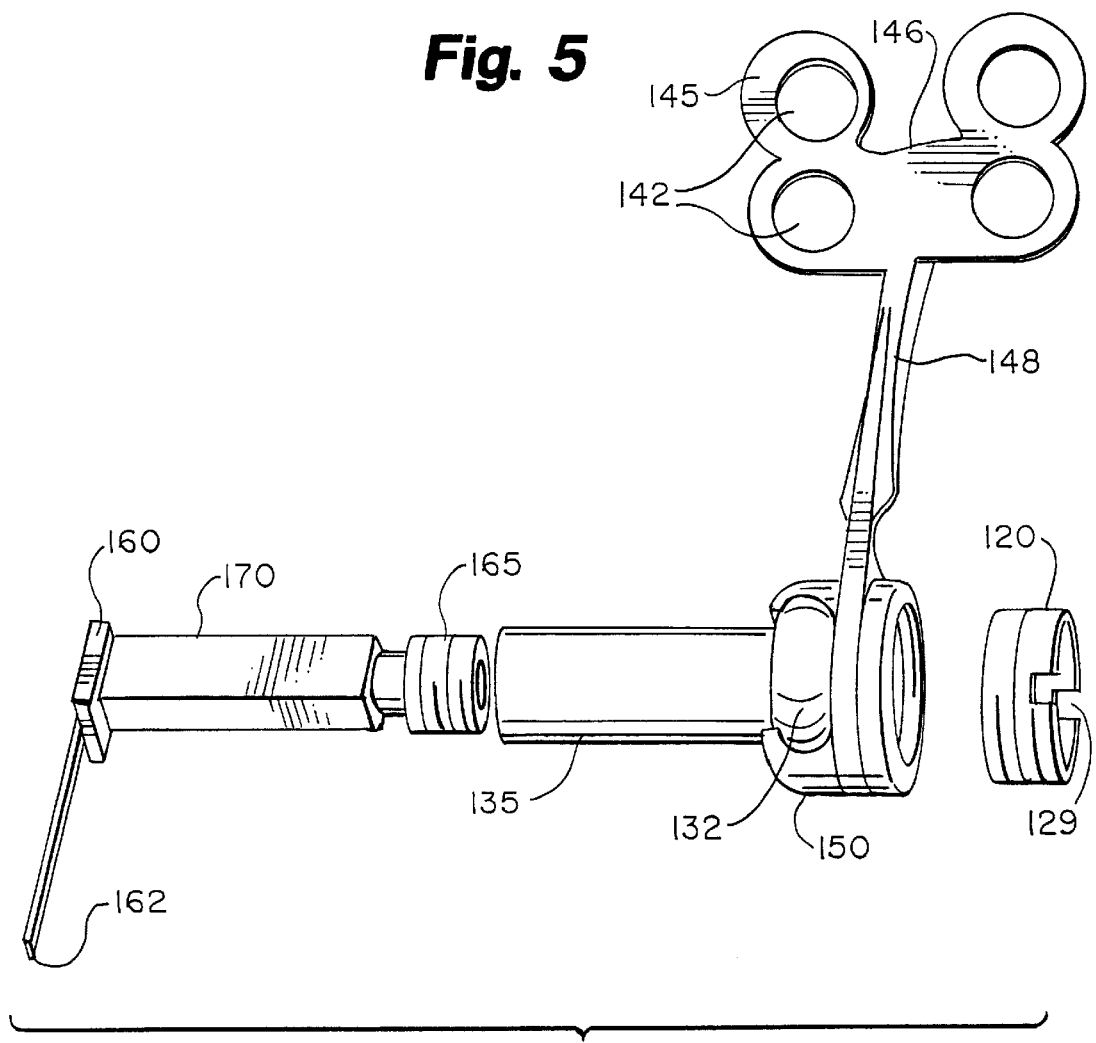
FIG. 5 shows a further view of the embodiment of FIG. 4 of the invention.

Referring to FIG. 1, ear 20 includes outer ear 22, middle ear 24, and inner ear 26. Outer ear 22, in turn, includes pinna 30 and exterior auditory canal (external acoustic meatus) 32. The exterior auditory canal extends through mastoid 34.

Middle ear 24 begins at tympanic membrane 36, the interior terminus of exterior auditory canal 32, and includes tympanic membrane 36 and ossicular chain 38. Ossicular chain 38, in turn, includes malleus 42, incus 44, and stapes 46.

FIG. 1 illustrates a frontal section of a human ear. Sound waves are directed into external auditory canal 32 by pinna 30. Frequency characteristics of the sound waves are preferably modified by the resident characteristics of external auditory canal 32. The sound waves impinge upon tympanic membrane 36, interposed at the terminus of external auditory canal 32, thereby producing mechanical tympanic vibrations. The mechanical energy of the tympanic vibrations is communicated by a series of articulating bones located in middle ear 24 to inner ear 26, comprising cochlea 88, vestibule 90, and semicircular canals 92. The series of articulating bones is referred to generally as ossicular chain 38. Thus, tympanic membrane 36 transforms acoustic energy in external auditory canal 32 to mechanical energy and ossicular chain 38 conveys the mechanical energy to cochlea 88. The hearing aid system comprising this invention assists the human auditory system in converting acoustic energy contained within sound waves into electrochemical signals delivered to the brain and interpreted as sound.

As best seen from FIG. 2, malleus 42 includes head 52, lateral process 54, anterior process 56, and manubrium 58. Malleus 42 attaches to tympanic membrane 36 at manubrium 58. Incus 44 articulates with malleus 42 at incudomalleolar joint 62 and includes body 64, short crus 66, and long crus 68. Stapes 46 articulates with incus 44 at incudostapedial joint 72 and includes posterior crus 74, anterior crus 75, capitulum 76, and base (front plate) 79. Capitulum 76 of stapes 46, in turn, includes head 77 and neck 78.

Base 79 of stapes 46 is disposed in and against a portion of inner ear 26. Inner ear 26 includes cochlea 88, vestibule 90, and semicircular canals 92. Base 79 of stapes 46 attaches to a membrane covered opening between cochlea 88 and middle ear 24 referred to as oval window 98. Oval window 98 is considered part of cochlea 88.

Normally, prior to implantation of the invention, tympanic vibrations are mechanically conducted through malleus 42, incus 44, and stapes 46 to oval window 98. Vibrations at oval window 98 are conducted into the fluid filled cochlea 88. Pressure is generated in cochlea 88 by fluidic motion accompanied by a second membrane covered opening in cochlea 88. The second membrane covered opening between cochlea 88 and middle ear 24 is referred to as round window 102. Round window 102 is also considered part of cochlea 88. Receptor cells in cochlea 88 translate the fluidic motion into neural impulses which are transmitted to the brain and perceived as sound. However, various disorders of tympanic membrane 36, ossicular chain 38, and/or cochlea 88 can disrupt or impair normal hearing.

For example, hearing loss due to damage in cochlea 88 is referred to as sensorineural hearing loss. Hearing loss due to an inability to conduct mechanical vibrations through middle ear 24 is referred to as conductive hearing loss. Other problems occur for some patients who have ossicular chains 38 which lack resiliency. Ossicular chains 38 with insufficient resiliency are either inefficient or totally fail to transmit mechanical vibrations between tympanic membrane 36 and oval window 98. As a result, fluidic motion in cochlea 88 is attenuated and receptor cells in cochlea 88 fail to receive adequate mechanical stimulation. Damaged or missing elements of ossicular chain 38, of course, may further interrupt transmission of mechanical vibrations between tympanic membrane 36 and oval window 98.

Various techniques have been developed to remedy hearing loss resulting from conductive or sensorineural hearing loss. For example, tympanoplasty is used to surgically reconstruct tympanic membrane 36 and establish ossicular continuity from tympanic membrane 36 to oval window 98. Various passive mechanical prostheses and implantation techniques have been developed in connection with reconstructive surgery of middle ear 24 for patients with damaged elements of ossicular chain 38. Two basic forms of prostheses are available: total ossicular replacement prosthesis, which is connected between tympanic membrane 36 and oval window 98; and partial ossicular replacement prosthesis, which is positioned between tympanic membrane 36 and stapes 46.

Different types of hearing aids have been developed to compensate for hearing disorders. A conventional "air conduction" hearing aid is sometimes used to overcome hearing loss due to sensorineural cochlear damage or mild conductive impediments to ossicular chain 38. Conventional hearing aids utilize microphones which transduce sound into an electrical signal. Amplification circuitry amplifies the electrical signal. A speaker transduces the amplified electrical signal into acoustic energy transmitted to tympanic membrane 36. In such systems, however, some of the transmitted acoustic energy is typically detected by the microphone, resulting in a feedback signal which degrades sound quality. Conventional hearing aids also often suffer from a significant amount of signal distortion.

Implantable hearing aid systems have also been developed, utilizing various approaches to compensate for hearing disorders. A variety of inner ear and middle ear implantable hearing aid systems have been designed. Implantation of a hearing aid system within the middle ear is particularly advantageous for various reasons. Importantly, placement of the system within the middle ear serves the purpose of shielding the device from damage caused by an impact to the head in general, or the ear specifically. Such a blow may have deleterious effects on the operability of the system or worse, such as when such a blow induces mechanical or vibratory consequences causing damage to one or more components of the inner ear. Another advantage of middle ear implantation is the ability to provide the patient with a system having no external components to address the issue of cosmetic concerns, including the lessening of any feelings of embarrassment or self-consciousness. Other advantages of middle ear implantation exist and can be readily appreciated by one skilled in the art.

A cochlear implant is an electronic device that allows profoundly deaf people to "hear" by electrical stimulation of the auditory nerve fibers within the inner ear. A typical system includes an external microphone, signal processor, and transmitter, and an implanted receiver and electrode. The microphone transponds normal sound waves, converting this mechanical sound energy into electrical energy representative thereof. The processor amplifies the electrical energy, filters it and sends it to the transmitter, which changes the electrical signals into magnetic signals. Transcutaneous magnetic currents cross the skin and are received by the implanted receiver, a coil for example, and the signal travels to the cochlea via a wire electrode. Current flows between this active electrode and a nearby ground electrode, preferably disposed in the eustachian tube, to stimulate nerve fibers present in the cochlea. The brain interprets this stimulation as sound.

A particularly interesting class of hearing assistance systems includes those that are configured for disposition principally within middle ear 24. In middle ear implantable hearing aids, an electrical-to-mechanical output transducer couples mechanical vibration to ossicular chain 38, which is optionally interrupted to allow coupling of the mechanical vibrations to ossicular chain 38. Both electromagnetic and piezoelectric output transducers have been used to effect mechanical vibrations upon ossicular chain 38.

One example of a partial middle ear implantable hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to incus 44. Such electromagnetic output transducers have relatively high power consumption, which severely limits their usefulness in total middle ear implantable hearing aid systems.

A piezoelectric output transducer is also capable of affecting mechanical vibrations to ossicular chain 38. An example of such a device is disclosed in U.S. Pat. No. 4,729,366, issued to Schaefer. Therein, a mechanical-to-electrical piezoelectric input transducer is associated with malleus 42, transducing mechanical energy into an electrical signal, which is amplified and further processed. A resulting electrical signal is provided to an electrical-to-mechanical piezoelectric output transducer that generates a mechanical vibration coupled to a separate element of ossicular chain 38 or to oval window 98 or round window 102. Ossicular chain 38 is interrupted by removal of incus 44. Removal of part of the ossicular chain prevents the mechanical vibrations delivered by the piezoelectric output transducer from mechanically feeding back to the piezoelectric input transducer.

Piezoelectric transducers have several advantages over electromagnetic transducers. The smaller size of the piezoelectric transducer advantageously eases implantation into middle ear 24. The lower power consumption of the piezoelectric transducer is particularly attractive for total middle ear implantation hearing aid systems, which may include a limited-longevity implanted battery as a power source.

A piezoelectric transducer is typically implemented as a ceramic piezoelectric bi-element transducer, which is frequently a cantilevered double-plate ceramic element in which two plates are bonded together such that they amplify a piezoelectric action in a direction approximately normal to the bonding plane. Such a bi-element transducer vibrates according to a potential difference applied between two bonded plates. A proximal end of such a bi-element transducer is typically cantilevered from a transducer mount which is secured at a reference point to a non-ossicular chain bone within the middle ear. A distal end of such a bi-element transducer couples mechanical vibrations to an ossicular element such as stapes 46.

Securing a bi-element transducer mount to the temporal bone adds invasive complexity to the surgical implantation procedure. Given the delicate nature of the middle ear, placement of the system at its proper position and with the appropriate level of pressure on the auditory element is critical. Failure to account for small dimensional anatomical variations among patients can have considerable consequences, supplying the difference between acceptable and poor hearing ability for a patient. Although piezoelectric transducers provide many advantages, the invention contemplates use of other types (e.g., electromechanical) of transducers.

Implantation of components of an implantable or partially implantable hearing assistance system typically involves gaining physical access to middle ear 24. This access is necessary for the purpose of implanting the transducers. These transducers can be sensors, drivers, microphones, or other components. Sensors and drivers commonly contact at least one of the bones of ossicular chain 38 within middle ear 24. The contact must be secure to insure that during the life of the hearing assistance system, appropriate physical contact is maintained between the transducer and the bone. Thus, the anchoring of a transducer within middle ear 24 is vital to the operation of this type of hearing assistance system. If physical contact between the target bone and the transducer is either lost or sporadic, the hearing assistance system cannot perform adequately. This poses a challenge for the surgeon, created not only by the surgical procedure, but by the anatomical differences found among patients. Because of both surgically created and naturally occurring morphological variations likely to be encountered within any given implantation area, flexibility and adaptability in the mounting and adjusting of the transducer is important for safe and effective implantation.

Figure 23:
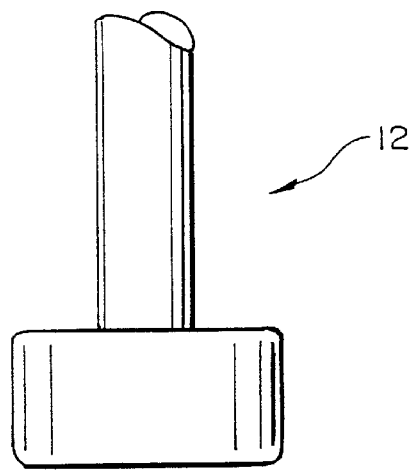
FIG. 23 is a view of a burr used in mastoidectomy.

The surgical procedure commonly used to gain physical access to middle ear 24 is called a basic or simple mastoidectomy. Because this procedure gives only limited access to middle ear 24, it is common to follow the mastoidectomy with a procedure to further open facial recess 15. These procedures are performed with various surgical tools, which include burr 12 and diamond burr (not shown). Burr 12, as depicted in FIG. 23, is a spherical boring instrument that removes bone and bony structures. As can be appreciated, the shape of the instrument dictates the shape of the area of the bone that remains after bone is removed. Often the mastoidectomy commences with the largest burr 12 available. As the implantation area becomes smaller, burr 12 size decreases accordingly. Diamond burr (not shown) is used for fine removal of anatomical structure. The use of different size burrs 12 creates layers of bone with a series of concave layers, with the shape of each layer generally dependent upon the size and shape of burr 12 used.

The mastoidectomy is initially performed with a large cutting burr 12, as well as suction, irrigation and other devices. The size of the burr typically decreases as depth into mastoid bowl 35 increases. During the initial steps of the procedure, the primary goal is to identify landmarks that allow the surgeon to maintain orientation while drilling. An initial cut with burr 12 is normally made along the temporal line while a subsequent cut is made substantially perpendicular to the first cut, and toward mastoid tip 33. These two lines intersect just posterior to the spine of henle 27. Initially, this region, called the supra medial triangle of Macewen 29, is the deepest part of the dissection and actually overlies the mastoid atrium 37. Using these first two cuts with the burr as general boundaries, the mastoid cortex bone is then removed in a systematic fashion referred to as saucerization. Saucerization of the cortex continues while landmarks are identified to maintain orientation. Wide saucerization is important in this procedure because insufficiently wide saucerization may result in inadequate recognition of landmarks and thus perhaps a less desirable exposure to the implantation area upon deeper dissection. It is this initial wide saucerization, followed by the narrowing of the dissection area, that creates one of the many challenges faced by the surgeon in mounting transducers and transducer support brackets, and which contributes to the need for minimizing any further tissue trauma beyond that necessary.

Important landmarks that the surgeon is looking for, during progressive cavity saucerization, are posterior bony canal wall 40, tegman 48 and sigmoid sinus 50. Care must be taken in this region because of the presence of facial nerve 17. Typically, digastic ridge 60 is identified and preserved as a landmark to facial nerve 17. Facial nerve 17 lies roughly on a line between the anterior tip of digastic ridge 60 and the lateral extent of the horizontal canal. In normal anatomy, facial nerve 17 lies directly inferior and medial to fossa incudis 70 as it finishes its tympanic segment. Once facial nerve 17 is identified, the air cells near facial nerve 17 can be safely removed with the smaller-sized diamond burr (not shown).

Mastoid 34 contains air cells that will be encountered during the dissection. The air cells, as mentioned above, are also typically present in the area of facial nerve 17, as well as in other areas of the dissection. In some countries, the above described procedure typically attempts to achieve the removal of all, or a significant amount of, the air cells so that a more firm bony structure is revealed. The more firm bony structure is a preferred mounting area for a transducer, or transducer support member. However, in other areas of the world, removal of a significant amount of the air cells of mastoid 34 are not typically effected during the simple mastoidectomy, resulting in further challenges to finding a secure mounting site.

The air cells, particularly near facial nerve 17, are removed; and the bone overlying sigmoid sinus 50 and tegmen 48 is thinned, which typically completes the mastoidectomy. Structures visible at this juncture normally include, among others, the head of incus 44 and a narrow buttress supporting the short process of incus 44.

Drilling of facial recess 15 is then normally performed, as the simple mastoidectomy typically does not expose sufficient areas of middle ear 24 to allow for transducer implantation. Again, burr 12 is used initially, with finer dissection performed by diamond burr (not shown). Facial recess 15 is opened until access to middle ear 24 is achieved. The use of burr 12 and diamond burr (not shown) and the gradual dissection of the bony areas in and around middle ear 24 result in irregularly shaped surfaces when the procedure is complete. A small generally triangular space is the result with the main trunk of facial nerve 17 forming the medial wall to this area. This area is normally large enough to attempt implantation, however, it is not uncommon for further surgical dissection to occur to optimally configure the area for access.

Figure 24:
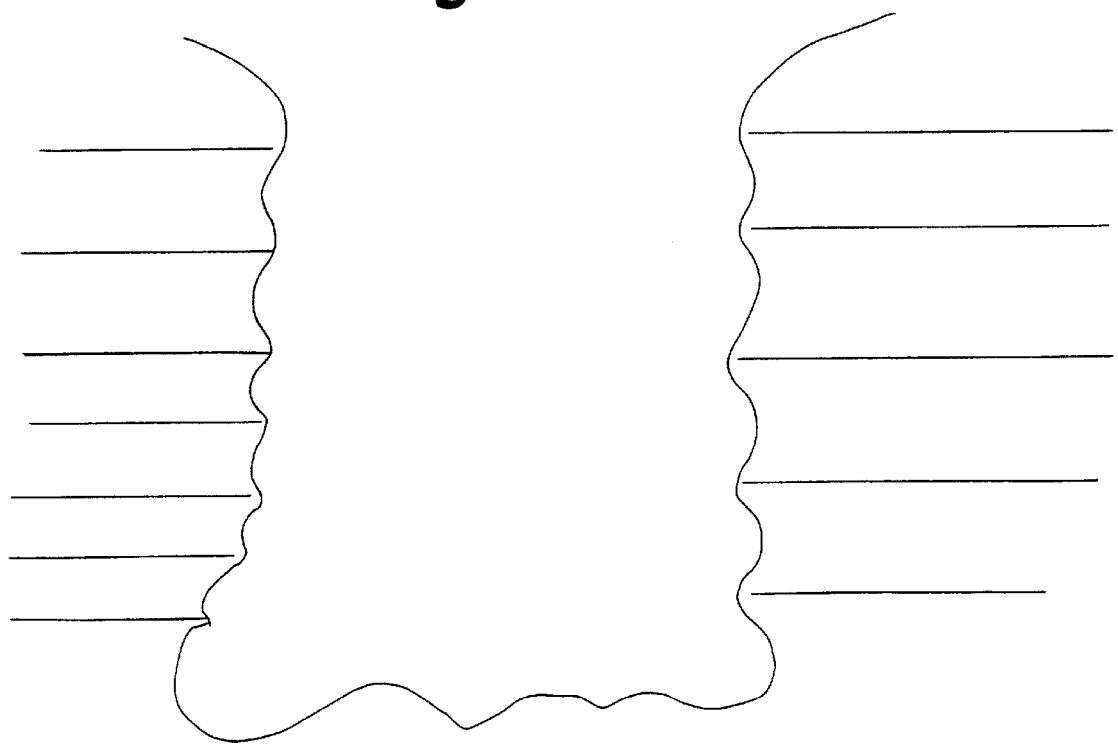
FIG. 24 is a view of the middle ear region after mastoidectomy.

The initial wide saucerization is followed by a more narrow saucerization of the area to accommodate facial nerve 17 and other vital structures within the implantation area. A slight widening out of the area once middle ear 24 is exposed, results in the formation of substantially convex-shaped walls within the implantation area. Further, these walls have been formed, as described above, by sweeping motions of spherical burr 12, thus creating concave layers in the walls of the implantation area. FIG. 24 depicts a view of one possible wall topography within the middle ear region, subsequent to completion of a mastoidectomy. The surgeon, then, with the goal of mounting a transducer within this area, faces multiple challenges. The irregular shape and non-planar of the walls of the implantation area make the connection between the apparatus and the target bone problematic. The naturally occurring differences in the anatomy found at the implantation site requires adaptability on the part of the surgeon, as well as the devices to be implanted. The promontory bone 175, for example, which is formed by the intrusion of the first turn of the cochlea 88 into the middle ear, yet is an obstacle the surgeon typically must work around to successfully implant a transducer and support member. The size and location of the promontory bone 175 is not identical in every patient. The variable surgically created shape of the implantation area, as well as the limited number of available implantation sites pose further challenges to the implantation surgery.

If the mounting of the transducer or support members thereof are to be completed successfully, the surgeon must be able to adapt to the conditions as discovered or created within the implantation area. It is this challenge that the various embodiments of the present invention address.

The invention provides a support assembly 10, shown in FIG. 3, and method for mounting a transducer within middle ear 24 or adjacent region. Different embodiments of the invention facilitate mounting to the surface of the cranium or, alternatively, to a bone mass adjacent to middle ear 24. In a preferred embodiment, support assembly 10 is mounted to a bone mass adjacent to the middle ear to shorten the mounting arm, thereby increasing the stability of support assembly 10 over a surface mount assembly. Through the many and varied features, the invention seeks to optimize proper positioning, adjustment, and placement of the device within middle ear 24.

The output transducer herein is referred to generally as a transducer 162. However, it should be recognized that transducer 162 may, alternatively, be either a driver (output transducer) or a sensor (input transducer). Referring to FIG. 3, one preferred embodiment of the invention consists of mounting flange 145 that is connected by neck 148 to hanger 150. Mounting flange 145 defines a plurality of apertures 142 for mounting the flange 145 within the implantation area. Mounting flange 145 is further characterized by offset 146 that enables different portions of mounting flange 145 to be disposed in different planes from one another, thereby facilitating mounting of support assembly 10 to irregular surfaces and enabling limited gross depth adjustments to be made at the mounting location. For example, variable contours of the implantation site might require one set of apertures 142 to be on a different plane than another set of apertures to get the desired mounting configuration. Offset 146 facilitates the resolution of this problem by providing a step-like feature in mounting flange 145.

Although references to bone screws and bone screw holes are made throughout this application, it should be recognized that these terms should not be taken as limiting the means by which the present invention can be attached in the implantation area. Alternative means of attachment include clips, staples, adhesives, rivets, or any other method known by one skilled in the art. Thus, though reference is generally made to mounting via bone screws, it is contemplated that other methods may be utilized to secure the invention within the implantation area.

Mounting flange 145 is bendable so that the portions of mounting flange 145 defining apertures 142 can be sufficiently positioned against mastoid 34, or other location within the ear, for secure mounting. Mounting flange 145 is preferably constructed such that excess material surrounding apertures 142 is removed. Construction of mounting flange 145 in this manner ameliorates obstruction, shaping, and fit problems associated with mounting support assembly 10 to irregular surfaces. Hanger 150 is preferably cylindrical in nature and is designed to accept retaining nut 120 at one end and ball end 139 of sleeve 135 at the other end. In the embodiment depicted in FIG. 3, sleeve 135 also defines sleeve bore 132 designed to mate with spinner 165 of transducer assembly 168. In one embodiment, transducer assembly 168 consists of threaded spinner 165, adjustable slide post 170, transducer support 160, and transducer 162. In this embodiment, hanger threads 157 are designed to accept retaining nut 120 that has external nut threads 125. Retaining nut 120 also defines bore 126 that has an inner spherical radius designed to mate with ball end 139 of sleeve 135. Retaining nut 120 is screwed into hanger 150 by engaging external nut threads 125 with hanger threads 157. The spherical inner radius of bore 126 of retaining nut 120 engages ball end 139 of sleeve 135. By tightening retaining nut 120 using slots 129, retaining nut 120 is forced down upon ball end 139 of sleeve 135, disposing ball end 139 against socket 152 of hanger 150, and securing ball end 139 of sleeve 135 in position. The design of retaining nut 120, hanger 150, and sleeve 135 are such that retaining nut 120 can be torqued down upon to stably secure sleeve 135 within the implantation area, providing security so that retaining nut 120 does not back out after implantation. It is contemplated that a number of torque settings would be available depending upon multiple factors—including the length of time the retaining nut would be required to perform its function. This torquing feature of retaining nut 120 is useful to obviate a screw-loose scenario in the implantation area of the patient.

In one embodiment of the invention, to facilitate engagement of ball end 139 of sleeve 135 with hanger 150 at its receptacle opening 154, and to facilitate the rotating and pivoting of sleeve 135 once engaged in socket 152 of hanger 150, the surfaces of ball end 139 of sleeve 135, receptacle opening 154, and socket 152 of hanger 150 are coated with a material to reduce the coefficient of friction, such as polytetrafluoroethylene (PTFE) or other appropriate biocompatible material. This feature facilitates proper positioning of transducer 162 against a bone of ossicular chain 38, such as stapes 46.

Figure 10:
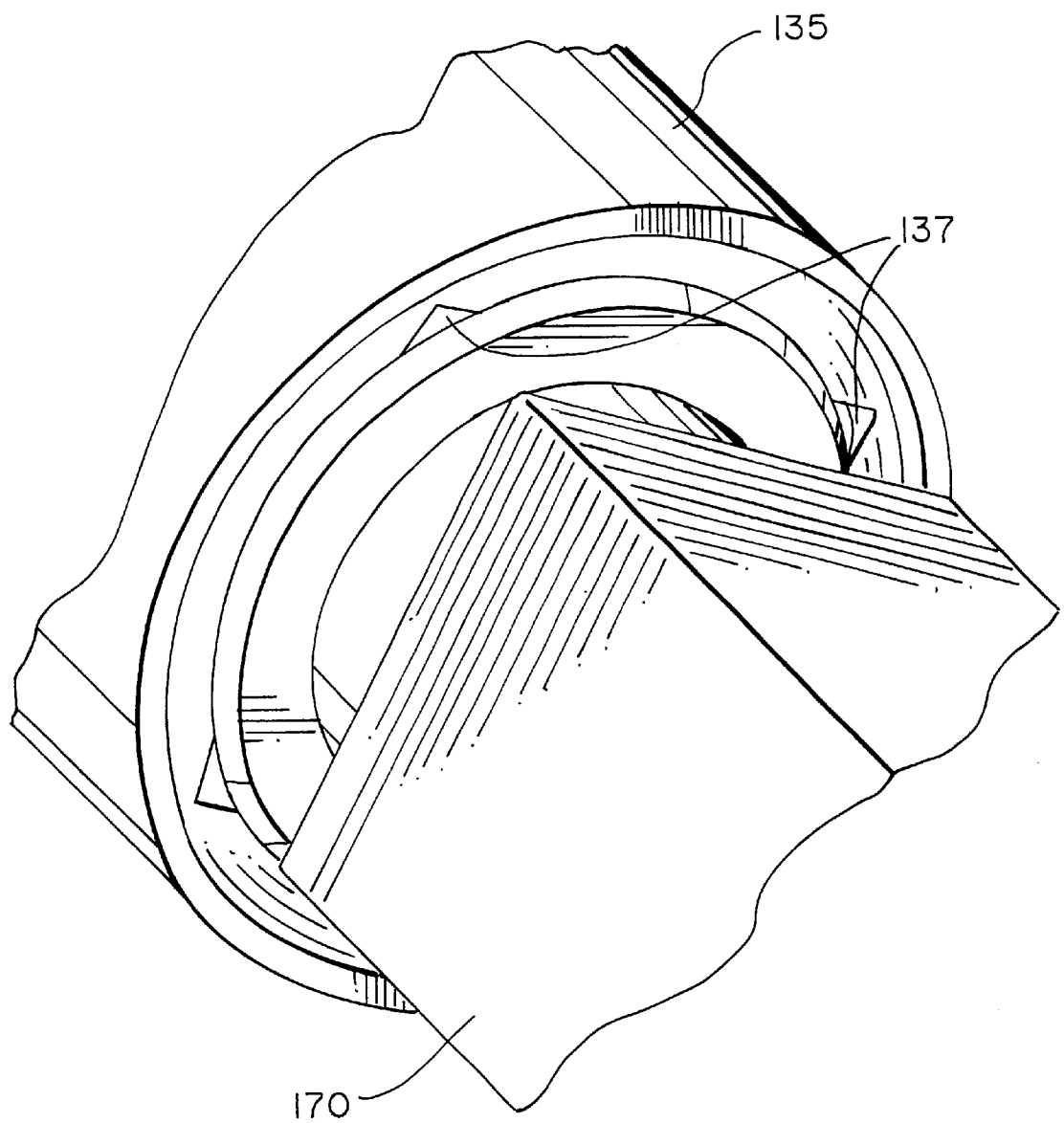
FIG. 10 is a detailed view of the engagement of the transducer assembly and the sleeve.

One preferred embodiment of the invention allows for the adjustment of the overall length of the portion of the invention formed by sleeve 135 and engaged transducer assembly 168. In this embodiment, spinner 165 is threaded to match the threaded portion of sleeve bore 132. Further, the inner diameter of bore 132, beginning at the second end of sleeve 135, is constructed with a predetermined number of V-cuts or notches 137, preferably four, to receive adjustable slide post 170, as depicted in FIG. 10. Spinner 165 can be moved through sleeve bore 132, and as it does so, adjustable slide post 170 can slide within sleeve 135, making the overall length of sleeve 135 and transducer assembly 168 adjustable. Because sleeve 135 and attached transducer assembly 168 can be removed from hanger 150, approximate adjustments can be made before mounting sleeve 135 within hanger 150. Further adjustment can be made while ball end 139 of sleeve 135 is engaged with socket 152 via retaining nut 120. Bore 126 allows access to the top portion of spinner 165 through sleeve bore 132 with the use of an appropriate tool. Thus, the overall length of sleeve 135 and transducer assembly 168 may be adjusted by rotating spinner 165, even while retaining nut 120 and sleeve 135 are attached to hanger 150. Linear adjustments made at transducer assembly 168 and transducer 162 are properly viewed as fine adjustments.

In one embodiment of the invention, transducer assembly 168 is coated with a material, such as a plastic or other suitable coating known to one of skill in the art, to restrain any wobbling motion that might be present when transducer assembly 168 and sleeve 135 are at, or near, full extension. The presence of the coating introduces a friction into the interface between sleeve 135 and transducer assembly 168 to aid in maintaining the spatial relationship therebetween without a backlash, subsequent to fine adjustment and positioning.

A further embodiment of the preferred invention facilitates rotational and angular adjustments of transducer 162 by virtue of the "ball-and-socket" nature of the coupling between sleeve 135 and hanger 150. As stated above, linear movement of transducer 162 within the implantable area is also possible by adjusting the length of adjustable slide post 170 within sleeve 135, by means of adjusting spinner 165. This angling feature is depicted in FIG. 4 where depicted angle 115 is greater than 90 degrees.

In a further embodiment of the invention, sleeve 135 is available in a selectable variety of lengths, to accommodate the surgical and natural morphological differences encountered within the implantation area. Further, adjustable slide post 170 comprises a selectable number of assemblies of different sizes and configurations to facilitate in the mounting and adjustment of this invention. The interchangeability of the variety of different-sized sleeves 135 and adjustable slide posts 170 serves to increase flexibility for the surgeon during implantation in response to morphological variations among patients.

Figure 6:
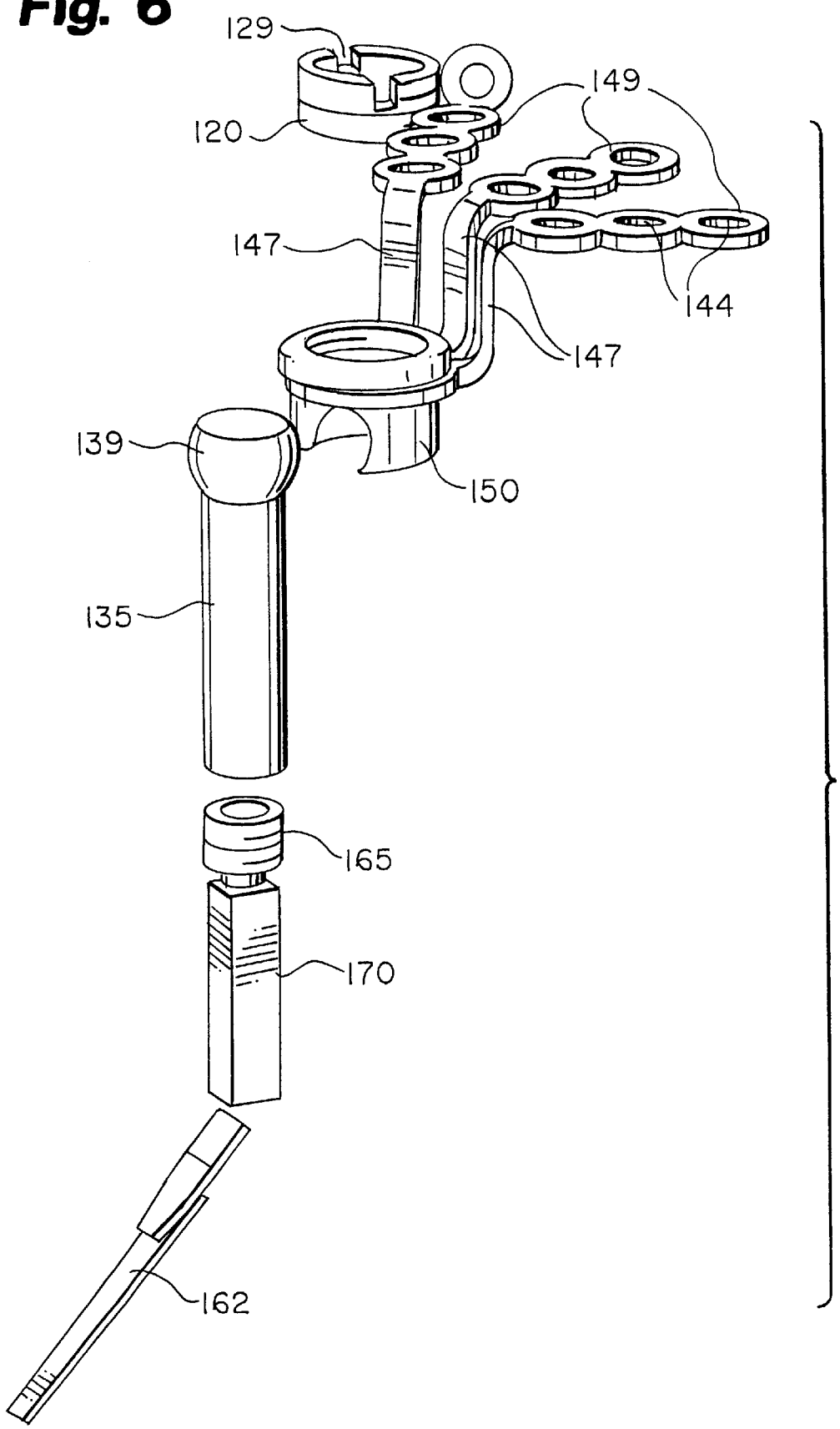
FIG. 6 depicts another embodiment of the invention wherein multiple mounting flanges and multiple neck portions are attached to the hanger along with a further embodiment of the transducer portion.

Another embodiment of the invention is depicted in FIG. 6. This embodiment possesses multiple mounting flanges 149 each being connected by neck 147 to hanger 150. Mounting flanges 149 are flexible to allow for bending and to position apertures 144, facilitating ease of placement of the invention by the surgeon in the implantation area. A representation of the flexible nature of mounting flanges 149 is depicted in FIG. 6, in which the flanges are shown as not co-planar. Alternatively, mounting flanges 149 and necks 147 may be removed, for example by snipping off or otherwise removing one or more of flange 149 and neck 147, if unnecessary for mounting support assembly 10. Further, neck 147 and neck 148 may also be flexible or semi-rigid to allow even more options to the implantation surgeon in mounting the support members and transducers.

Figure 11:
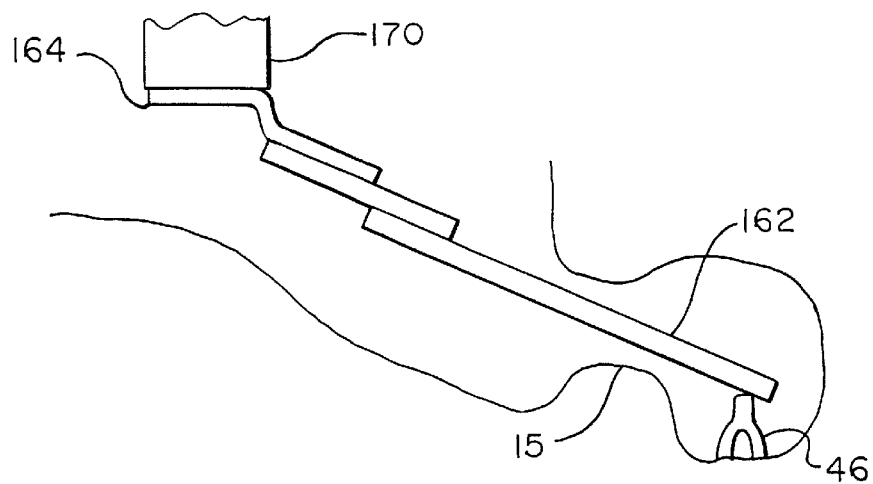
FIG. 11 is a representative view of the transducer engaging the stapes as viewed through a facial recess.
Figure 12:
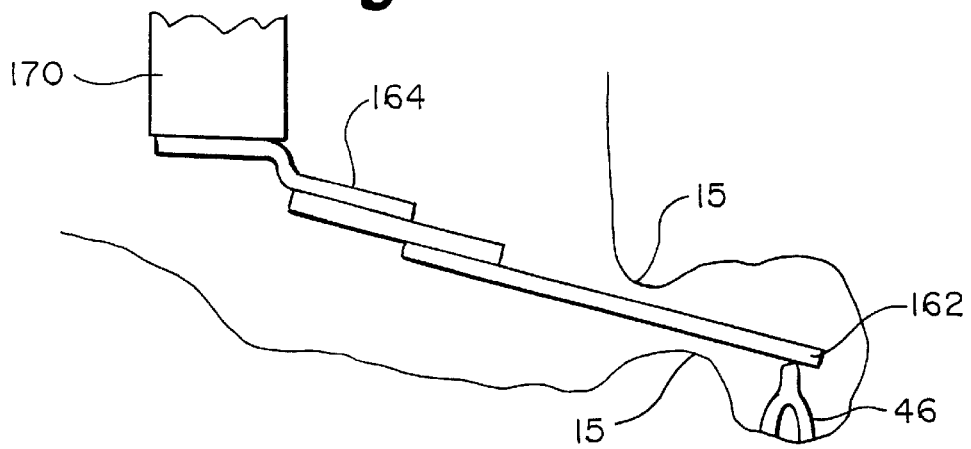
FIG. 12 is a view similar to that of FIG. 11, but depicting the transducer at an angle of introduction different from that of FIG. 11.

One embodiment of the invention possesses a feature to allow for the adjustment of transducer 162 by means of semi-rigid bendable member 164, shown in FIG. 7 and FIG. 8. Bendable member 164 is affixed to transducer support 160 at a first end, and is firmly affixed to and supports transducer 162 at a second end. By means of bendable member 164, transducer 162 can be angled to permit alignment of the distal end of transducer 162 with the target anatomical structure within ear 20. FIGS. 11 and 12 illustrate this feature of the invention. As depicted in FIG. 11, facial recess 15 requires transducer 162 to be placed at a steeper angle with respect to adjustable slide post 170. FIG. 12 depicts facial recess 15 that requires a more shallow angle between adjustable slide post 170 and transducer 162 to make operable contact with stapes 46. In each instance, bendable member 164 facilitates this task.

A variation of this embodiment includes adjustable slide post 170 which is selectable from a plurality of adjustable slide posts, and wherein post 170 may have a bendable member 164 positioned at a different preset angle at the connection point between post 170 and transducer 162. This feature enables fine adjustments for positioning transducer 162 against a bone of ossicular chain 38, such as stapes 46, rather than relying on merely crude adjustment mechanisms and methods to achieve functional relation between the transducer and the ossicle. Further, post 170 can be constructed from a material with sharable properties to allow the end of post 170, where the transducer support 160 is attached, to be shared to allow another means to anole transducer 162 for proper positioning.

Figure 13:
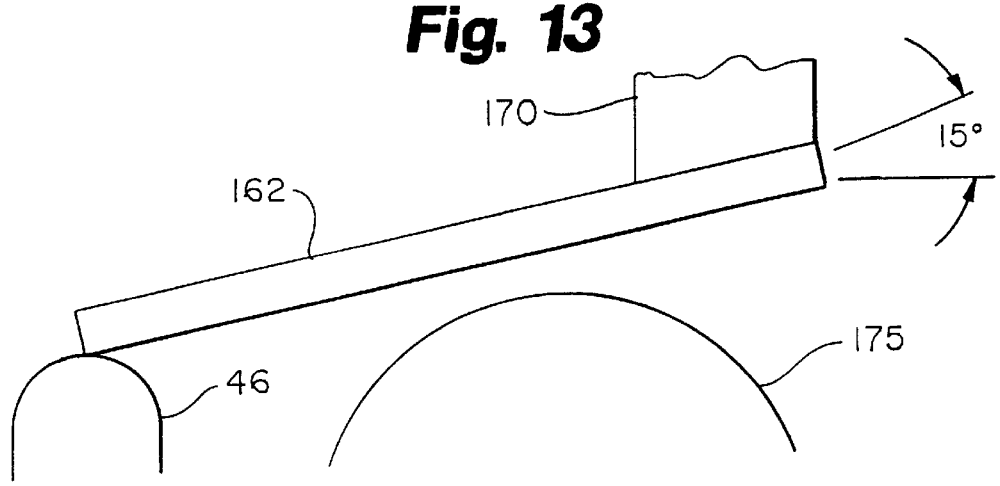
FIG. 13 is a detailed view depicting placement of a transducer against an auditory element while avoiding contact with a separate bone structure of the patient.

Another instance wherein it is necessary to position transducer 162 at an angle from its engagement with sleeve 135 is when promontory bone 175 is positioned particularly close to stapes 46. In this situation, it is necessary to mount transducer 162 angularly from adjustable slide post 170. An angle of descent near or at 15° from the plane defining the distal end of post 170 is preferable to ensure that transducer 162 does not engage promontory bone 175, as shown in FIG. 13.

Referring now to FIG. 8, a close-up view is depicted of transducer assembly 168 with bendable member 164 and electrical contacts 111 configured to receive or send electrical signals. Further depicted is a detailed view of the construction of transducer 162, comprising driving board portion 113 and bendable portion 164.

In one preferred embodiment of the subject invention, spinner 165, sleeve 135 and other portions of support assembly 10 are constructed from biocompatible materials known to one of skill in the art, such as grade-5 titanium, gold or stainless steel 316-L, or other functional material. It is also anticipated that other materials, for example, an acetal resin, such as that manufactured under the trade name DELRIN®, may be used in construction of components of this invention.

A useful feature of the various embodiments of this invention is the ability to remove sleeve 135 with attached transducer assembly 168 from hanger 150 while mounting flange 145 or, alternatively, flanges 149 remain attached to bone. This feature allows for general sizing of transducer assembly 168 and sleeve 135 without the necessity of complete removal of support assembly 10, thus avoiding excess trauma, such as the possibility of stripping out the bone screw holes, thereby making remounting more difficult. This feature is also useful when replacing a previously mounted transducer assembly. The invention allows for the removal of sleeve 135 and transducer assembly 168 without disruption of mounting flange 145 or, alternatively, mounting flanges 149, thus preserving the mounting area from damage. The replacement of a transducer assembly 168 therefore is simplified.

Because sleeve 135 and transducer assembly 168 may be detached from hanger 150, a further embodiment of the invention contemplates temporary replacement of transducer assembly 168 with a sizing and positioning model (not shown) that may be substantially transparent, pliable, or both. Upon initial placement of transducer assembly 168 for sizing, the model facilitates placement of transducer 162 in relation to stapes 46 or other target bones within middle ear 24 of the patient. The transparent feature aids visualization during placement and allows the surgeon performing the implantation to better view potential obstructions in the implantation area and make necessary adjustments. The pliability of the model is advantageous from a safety perspective. The safety of the patient is maintained by protecting the delicate structure of middle ear 24 during positioning in general and during gross positioning specifically. Preservation of the integrity of transducer 162 is also maintained as any obstructions can be avoided based on information learned during the trial placement with the model. After general sizing has taken place, the model can then be replaced by an operable transducer assembly 168, and thereafter further adjustments can be made as described above.

A further embodiment of this invention provides a support assembly 205 for disposing an output transducer 310 within middle ear 24 for use in an implantable hearing aid system. Support assembly 205 is capable of two- and three-directional movement at a plurality of locations along its length.

Accompanying output transducer 310 as components of the hearing aid system are electronics unit 360 and input transducer (not illustrated), each of which is known in the art. Electronics unit 360 and input transducer may be implanted separately from output transducer 310. This further eases implantation, repair, and maintenance or adjustment to electronics unit 360, such as changing a battery, without the need for removing support assembly 205.

For implantation of system components, an access hole 85 is created in a region of the temporal bone, known as mastoid 34 through a mastoidectomy. An incision is made in the skin covering mastoid 34, and the underlying access hole 85 is created through mastoid 34, allowing external access to middle ear 24. The access hole is located approximately posterior and superior to external auditory canal 32. By placing access hole 85 in this region, output transducer 310, affixed to support assembly 205, can be placed on approximately the same planar level as the auditory element, such as stapes 46, which it engages.

Figure 14:
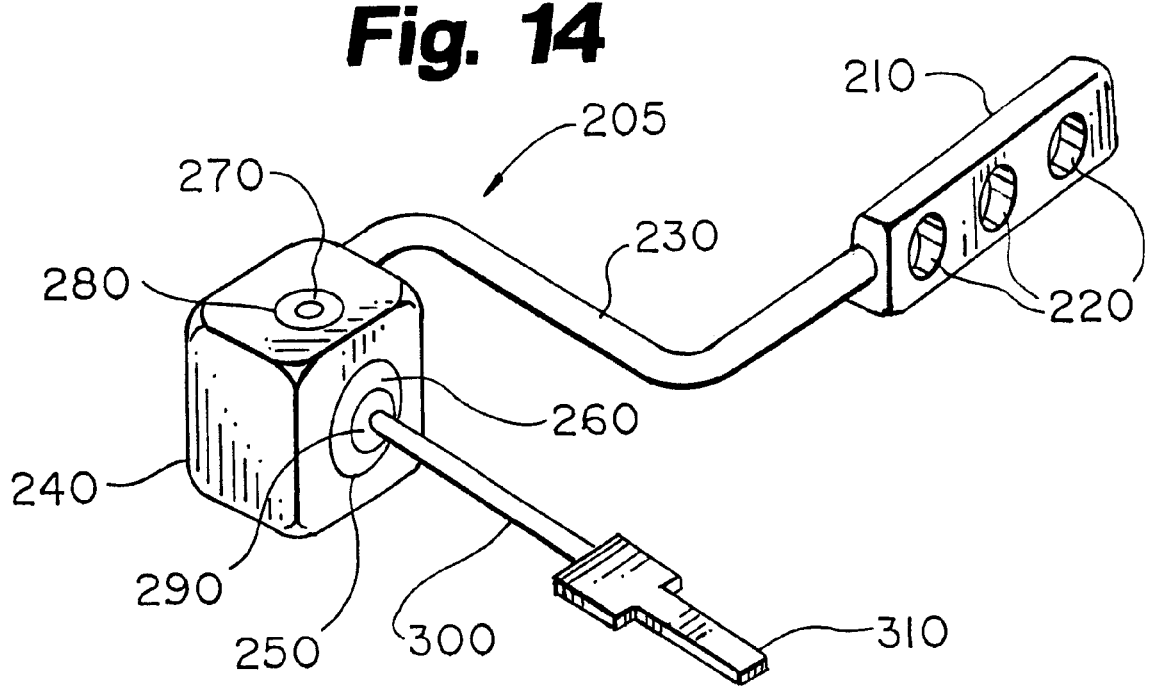
FIG. 14 is a perspective view of a further embodiment of the present invention.

In one embodiment, as shown in FIG. 14, support assembly 205 is implanted into middle ear 24 for mounting.

Support assembly 205 is mounted to a region of the temporal bone, preferably mastoid 34, by multiposition mounting plate 210. Mounting plate 210 is capable of being deformed to substantially conform to the anatomical features of the particular patient. As such, multiple configurations are possible, depending upon patient anatomy and other relevant factors. Mounting plate 210 has a number of apertures 220 positioned along its length, capable of receiving at least one bone screw 320. Bone screw 320 secures support assembly 205 to mastoid 34. The ability of mounting plate 210 to be deformed to substantially conform to the patient morphology enables the surgeon to place bone screw 320 at a preferred angle. In the event of a mastoidectomy, when the internal bone mass assumes a concave character with an attendant ledge, the bone screws 320 can be recessed and secured within the mastoidectomy topography. Bone screw 320 comprises any suitable biocompatible material, and preferably is self-tapping. Two preferred diameters for bone screw 320 are 1.2 mm and 1.7 mm. Support assembly 205 also comprises any suitable biocompatible material as is well-known to one skilled in the art. Bone screw 320 can also be any type of screw well-known to one skilled in the art, such as an orthopedic bone screw, a torx head screw, a single- or double-slotted head screw. To reduce the number of components handled during implantation and mounting of the invention, support assembly 205 is preferably adapted to receive and hold bone screw 320 such that the combination can be placed against mastoid 34 as a single unit. Any known technique, such as pre-threading or otherwise shaping support assembly 205 in accordance with known practices is suitable.

Positioned at one end of mounting plate 210 is extendible frame member 230. Frame member 230 is designed to be readily bendable at various positions along its length, as illustrated in FIG. 14 or otherwise. Bendable frame member 230 facilitates mounting of support assembly 205 to irregular surfaces and enables gross depth and positioning adjustments to be effected at the mounting site. Use of multiposition mounting plate 210 and bendable frame member 230 may obviate or limit the need for grinding the patient's mastoid 34 to effect placement of support assembly 205. Housing 240 is attached to the distal end of frame member 230. In one embodiment, the outer jacket of housing 240 encases a captured ball 260, which is free to rotate within housing 240. Captured ball 260 extends partially through a first housing orifice 250 located on a first side of housing 240 and connects to mounting rod 300 externally from housing 240. Captured ball 260 functions as a joint 290, or universal connector, such as a ball-and-socket-type joint, in conjunction with mounting rod 300. Utilization of a ball-and-socket-type joint allows three-way positioning of output transducer 310, including linear, rotational, and angular movement. Captured ball 260 may be an intact sphere or, alternatively, may be split into two substantially hemispherical portions operatively coupled to one another. A second housing orifice 280 is located on a second side of housing 240, through which locking screw 270 enters housing 240. Locking screw 270 may be advanced to a point where engagement with captured ball 260 is effected, thereby restricting movement of the ball-and-socket joint assembly. Mounting rod 300 extends outward from captured ball 260 and, at a distal end, is attached to output transducer 310. Mounting rod 300 is capable of linear movement to further assist in positioning output transducer 310. Output transducer 310, as a result of the angular, rotational, and linear movement, may be positioned with precision in a near-full range of positions in three-dimensional space.

Figure 15:
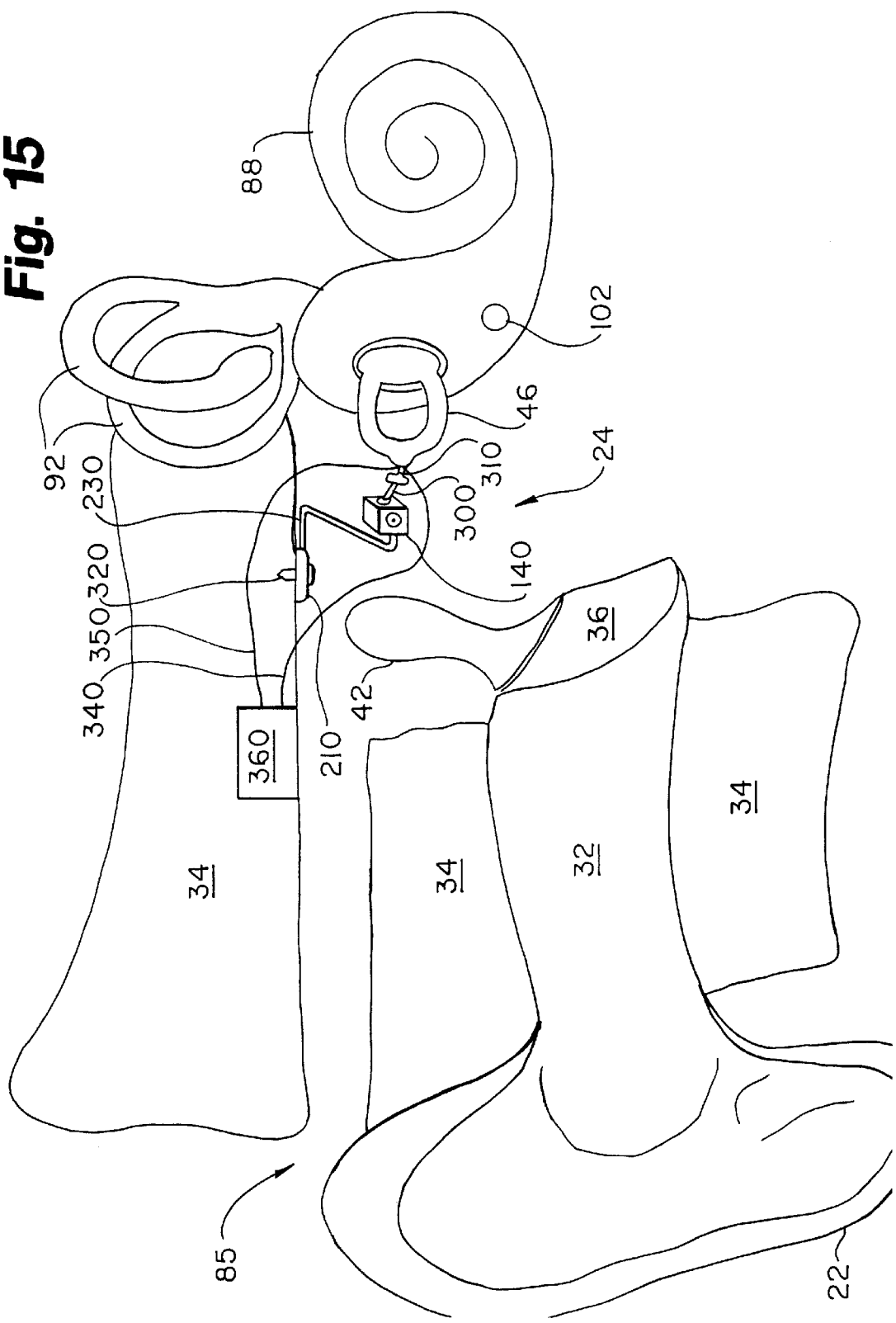
FIG. 15 is a view of a particular embodiment of the invention placed in operational position against an auditory element of the middle ear.
Figure 16:
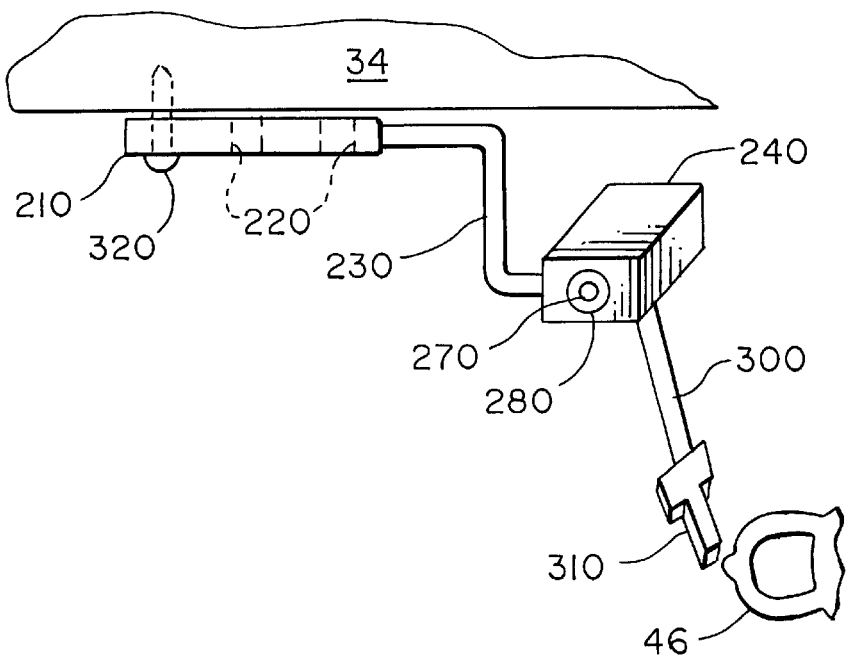
FIG. 16 is a detailed view of FIG. 15 illustrating the mounting of an embodiment of the invention to a portion of the temporal bone structure.

As best shown in FIGS. 15–16, support assembly 205 is mounted to mastoid 34, or other suitable temporal bone, and is then adjusted and manipulated at frame member 230, captured ball 260, and mounting rod 300, as necessary. Adjustments made at mounting plate 210 and frame member 230 may be characterized as gross adjustments. Adjustments made at captured ball 260 and mounting rod 300 are fine adjustments used to effect final placement, or docking, of output transducer 310 against a suitable auditory element, such as stapes 46 or malleus 42. In positioning output transducer 310 against an auditory element, it is important to join the two components against one another gently and carefully so as to avoid damage to anatomical structure or the hearing aid system. Failure to exercise proper care in positioning support assembly 205 may result in mechanical or electrical damage to output transducer 310 or physical trauma to the auditory element. As a result, the multiple adjustment mechanisms of support assembly 205, comprising both gross and fine adjustment mechanisms, play a substantial role in the overall effectiveness of the hearing aid system.

Referring now to FIG. 15, electrical lead wires 340, 350 extend from output transducer 310 and connect to electronics unit 360 at a separate location. Of course, an input transducer (not illustrated) must also be coupled to electronics unit 360 to receive incoming acoustical vibrations which are processed and forwarded to output transducer 310 to effect proper hearing.

In one particular embodiment, the invention is used in conjunction with a disarticulated ossicular chain 38. For example, incus 44 is removed from ossicular chain 38 to prevent feedback of mechanical vibration from output transducer 310 to the input transducer. By affixing support assembly 205 to mastoid 34 by bone screw 320 or other suitable fastener, mechanical vibrations of output transducer 310 are not transmitted back through support assembly 205.

Figure 17:
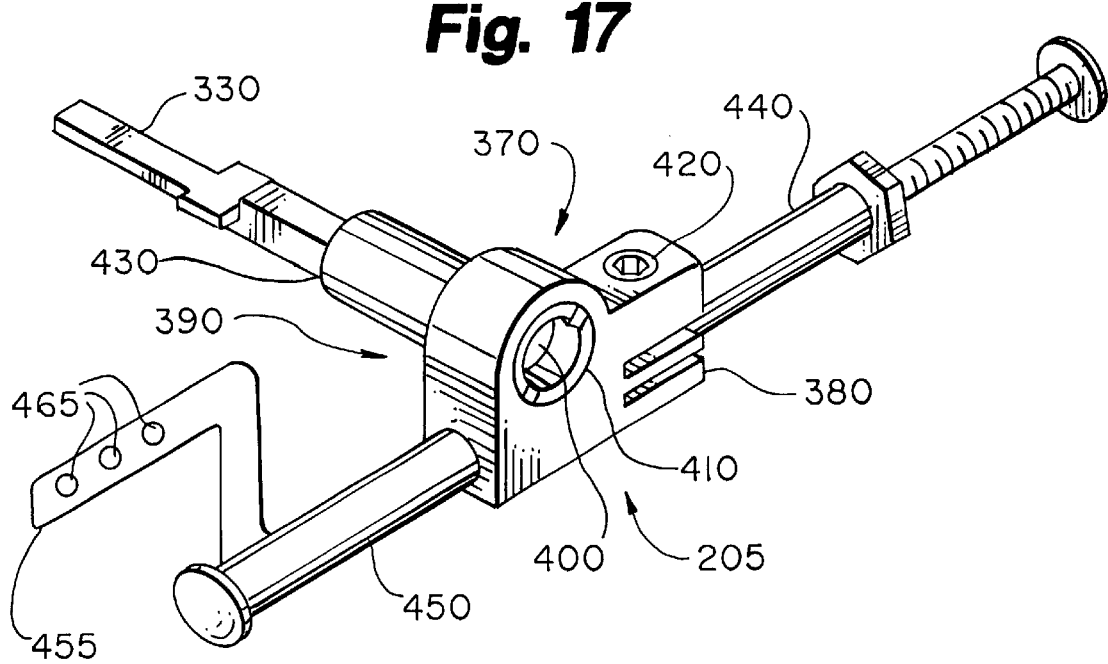
FIG. 17 is a perspective view of an embodiment of the present invention.

FIG. 17 illustrates an alternative embodiment of support assembly 205 in accordance with the present invention. Adjustable mounting bridge 440 and rigid mounting arm 450 operate in tandem to effectively mount support assembly 205. Mounting bridge 440 is linearly adjustable to effect a tension fit in middle ear 24 or adjacent cavity. Attached to mounting arm 450 and extending therefrom is mounting plate 455. Plate 455 has positioned along its length one or more apertures 465 adapted for receipt of a mechanical fastener. Importantly, plate 455 provides a tertiary affixation point with which to secure support assembly 205. The presence of plate 455 is preferable to obviate exertion of excessive pressure by mounting arm 450 against tegman 48, as such pressure is transferred directly to brain sacs posterior to tegman 48. Encasement 380 of housing 370 is positioned between bridge 440 and arm 450. Encasement 380 is further coupled to joint 390, preferably a three-way positional member, such as a ball-and-socket joint, to enable linear, angular and rotational positioning of transducer 330 against an auditory element of middle ear 24. Retaining nut 410 and set screw 420 function as adjustment/locking mechanisms and may be engaged with joint 390 to restrict angular and rotational movement of joint 390. Extension shaft 430 depends from joint 390 and is adapted for linear movement toward and away from housing 370 at joint 390. A third adjustment/locking mechanism, such as lead screw 400, is positioned about joint 390 to restrict linear movement of shaft 430 during positioning. Joint 390, like captured ball 260, may be intact or split.

Figure 21:
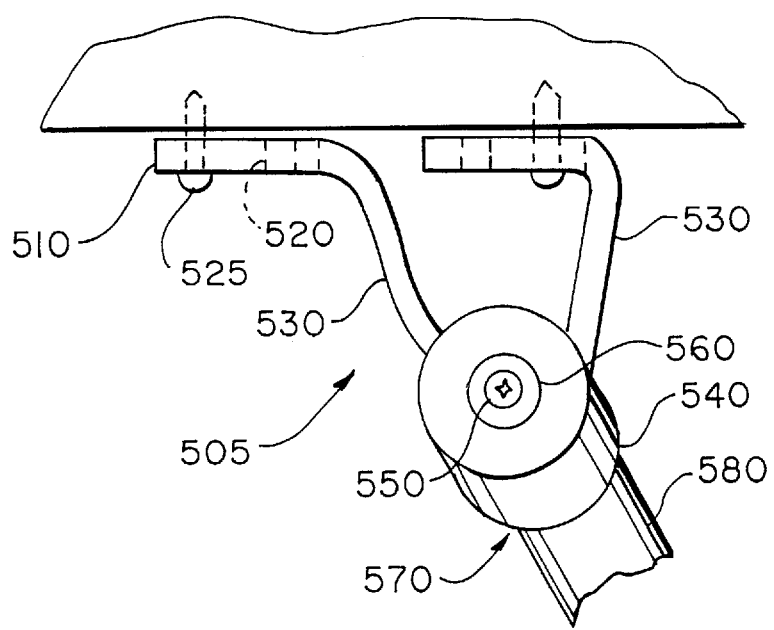
FIG. 21 is a detailed view of an embodiment of the invention mounted in a human ear.

In the embodiment as shown in FIG. 18, support assembly 505 is comprised of a pair of bendable, multiposition mounting tabs 510 by which support assembly 505 is mounted to mastoid 34, or other suitable temporal bone. Mounting tabs 510 are characterized by two or more apertures 520 for acceptance of mounting screw 525 or other suitable mechanical fastener as illustrated in FIG. 21. It is contemplated that either or both of the two apertures 520 on each of the two tabs 510 may be utilized to facilitate mounting support assembly 505 to irregular surfaces, thereby providing multiple mounting positions.

Mounting tabs 510 are attached to bendable mounting arms, such as frame members 530, which are commonly joined at shoulder 540. Frame members 530 are constructed to be readily bendable in order to facilitate positioning of the hearing aid system and provide still further configurations for support assembly 505. In one embodiment, as shown in FIG. 18, frame members 530 are characterized by offset 535 to allow support assembly 505 to be located below the outer surface of the head, thereby preventing damage to the assembly or the elements of the ear from an impact to the head or ear area. Mounting tabs 510 and frame members 530 are constructed of any suitable biocompatible material known in the art and are constructed to be readily deformed at multiple positions along their respective lengths. Again, the multiplicity of positioning adjustments may obviate or lessen the need for grinding the patient's mastoid 34 to effect placement of support assembly 505.

Figure 22A:
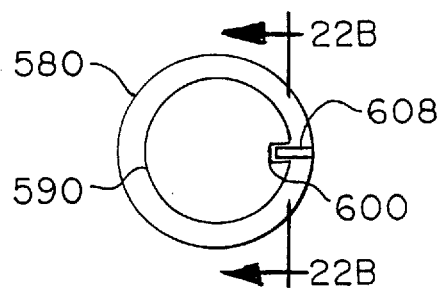
FIG. 22A is a cross-sectional view of FIG. 19 along line X—X.
Figure 22B:
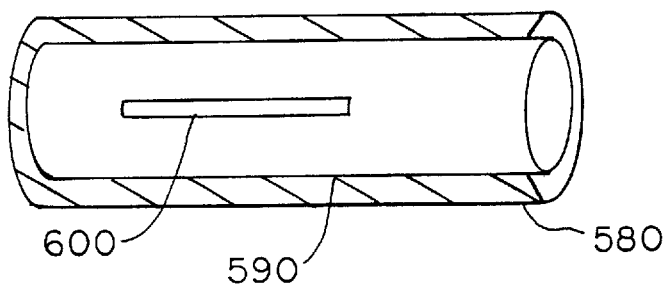
FIG. 22B is a cross-sectional view of FIG. 22A along line Y—Y.

Shoulder 540 engages joint 570, preferably a three-way positional member such as a ball-and-socket joint, to allow further angular and rotational movement of support assembly 505 to facilitate positioning of output transducer 545 against an auditory element of middle ear 24. Again, as with captured ball 260 and joint 390, joint 570 may assume the form of an intact sphere or two substantially hemispherical components operatively engaged. At the top portion of shoulder 540, a first retaining mechanism such as lead screw 550, is positioned which engages inner sleeve 590 to restrict or allow linear movement thereof. As shown in FIGS. 22A and 22B, inner sleeve 590 is housed within outer sleeve 580 and may be positioned to extend beyond the length of outer sleeve 580 by retraction of lead screw 550. Outer sleeve 580 and inner sleeve 590, in part, maintain their spacial relationship via slot 600 running a portion of the length of inner sleeve 590, which engages a pin 608 positioned toward the distal end of outer sleeve 580. Additionally, outer sleeve 590 and inner sleeve 580 may engage one another via mating internal-external threads (not shown). Angular and rotational movement of outer sleeve 580 and inner sleeve 590 is controlled at joint 570. Such movement may be limited or restricted by adjustment of a second retaining mechanism, such as retaining/locking nut 560, which may be positioned to engage joint 570 and is located atop shoulder 540.

Inner and outer sleeves 580, 590 together comprise a connector assembly or spacing shaft, from which pivot base 700 is positioned at the distal end of inner sleeve 580. Base 700 is free to rotate about the longitudinal axis of outer and inner sleeves 580, 590. Additionally, base 700 engages mounting rod 610 at pivot joint 620 to allow further rotational movement of mounting rod 610 about the axis of pivot joint 620. Positioned atop base 700 is rotational mounting rod set screw 615 to restrict and maintain the spacial position of mounting rod 610 during positioning of support assembly 505. Mounting rod 610 is capable of linear movement toward and away from base 700 at pivot joint 620. Linear mounting rod set screw 625 positioned atop pivot joint 620 restricts linear movement of mounting rod 610 during positioning of support assembly 505.

Output transducer 545 is affixed to the distal end of mounting rod 610. Upon mounting support assembly 505 at mounting tabs 510 to mastoid 34 or other suitable temporal bone, output transducer 545 is moved into position against an auditory element of middle ear 24, such as malleus 42, through a series of adjustments made to frame members 530, outer and inner sleeves 580, 590, base 700, and mounting rod 610.

Alternatively, in lieu of base 700, a further embodiment has flange 720 positioned between inner sleeve 590 and output transducer 545, as seen in FIG. 19. Output transducer 545 is capable of rotational movement about the longitudinal axis of outer and inner sleeves 580, 590. Due to the linear movement of inner sleeve 590 within outer sleeve 580, output transducer 545 may be further positioned in a linear manner.

Figure 25:
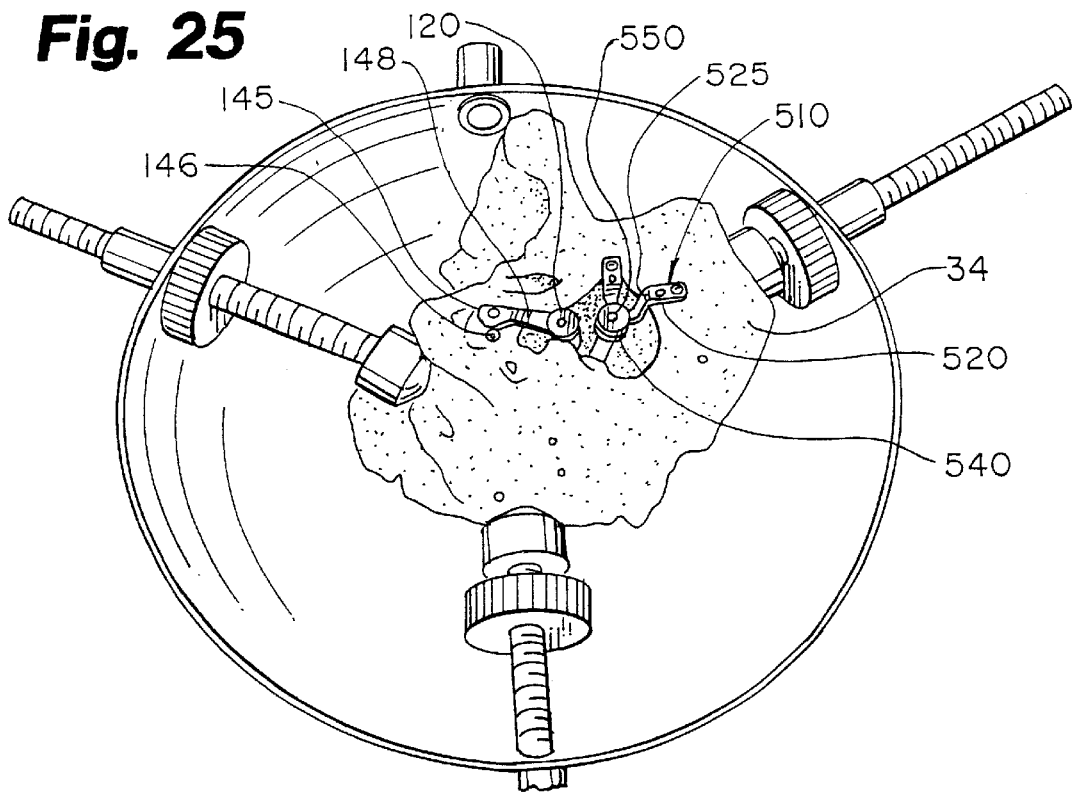
FIG. 25 is a view of an embodiment of the invention placed in operational position within a middle ear, exhibiting deformation of the mounting support.

A particular advantage of one embodiment of the present invention is the small volumetric profile of support assembly 505. Given the compact dimensions and the multiplicity of anatomical structures present in and around middle ear 24 and adjacent cavities, a small-volume profiled device is particularly advantageous. Because support assembly 505 may be deformed at mounting tabs 510 (refer to FIG. 25), frame member 530, about joint 570 and along outer and inner sleeves 580 and 590, support assembly 505 is able to assume a volumetric profile no larger than a volume defined by the widest cross-sectional area and length of support assembly 505. In the embodiment illustrated in FIG. 18, that profile would be defined in part by the cross-sectional area of shoulder 540.

Dimensional considerations are of great importance to address morphologic variations among patients. It is preferable to limit the dimensions of support assembly 505 as a whole and subparts thereof to enable implantation of assembly 505 within the small dimension of the middle ear region, and to account for varied anatomical requirements of the individual patient. For example, in a patient who has had a mastoidectomy, it is desirable to have a small-diameter outer sleeve 580 to prevent interference with the resulting bone side wall. Reduction of the footprint of transducer 545 would further assist in preventing such interference. In one embodiment, transducer 545 is reduced to dimensions such that transducer 545 extends only slightly beyond the profile defined by outer sleeve 580 at its distal end, thus minimizing the profile of support assembly 505.

Support assembly 505 is mounted to mastoid 34, or other suitable temporal bone, and is then adjusted and manipulated at frame members 530, joint 570, outer and inner sleeves 580, 590, base 700, and mounting rod 610, as necessary. Adjustments made at mounting tabs 510 and frame members 530 may be characterized as gross adjustments. Adjustments made elsewhere are more properly characterized as fine adjustments used to effect final placement, or docking, of output transducer 545 against a suitable auditory element, such as stapes 46 or malleus 42. In positioning output transducer 545 against an auditory element, it is important to adjoin the two components gently and carefully so as to avoid damage to anatomical structure or the hearing aid system. Failure to exercise proper care in positioning support assembly 505 may result in mechanical or electrical damage to output transducer 545 or physical trauma to the auditory element. The multiple adjustment mechanisms of support assembly 505, comprising both gross and fine adjustments, play an important role in the overall system effectiveness.

In particular patients, such as those who have had a mastoidectomy, frame members 530, mounting tabs 510, or both may need to be of extended length to facilitate proper positioning of support assembly 505. Frame members 530 may be further characterized by large sloping radii to provide sufficient support and to account for the additional space within middle ear 24 and adjacent regions as a result of the surgical removal of a portion of mastoid 34. Such an embodiment of the invention could be accomplished in a number of other ways readily apparent to one of skill in the art, including the introduction of a separate extension plate (not illustrated) at the proximal end of support assembly 505.

Figure 20:
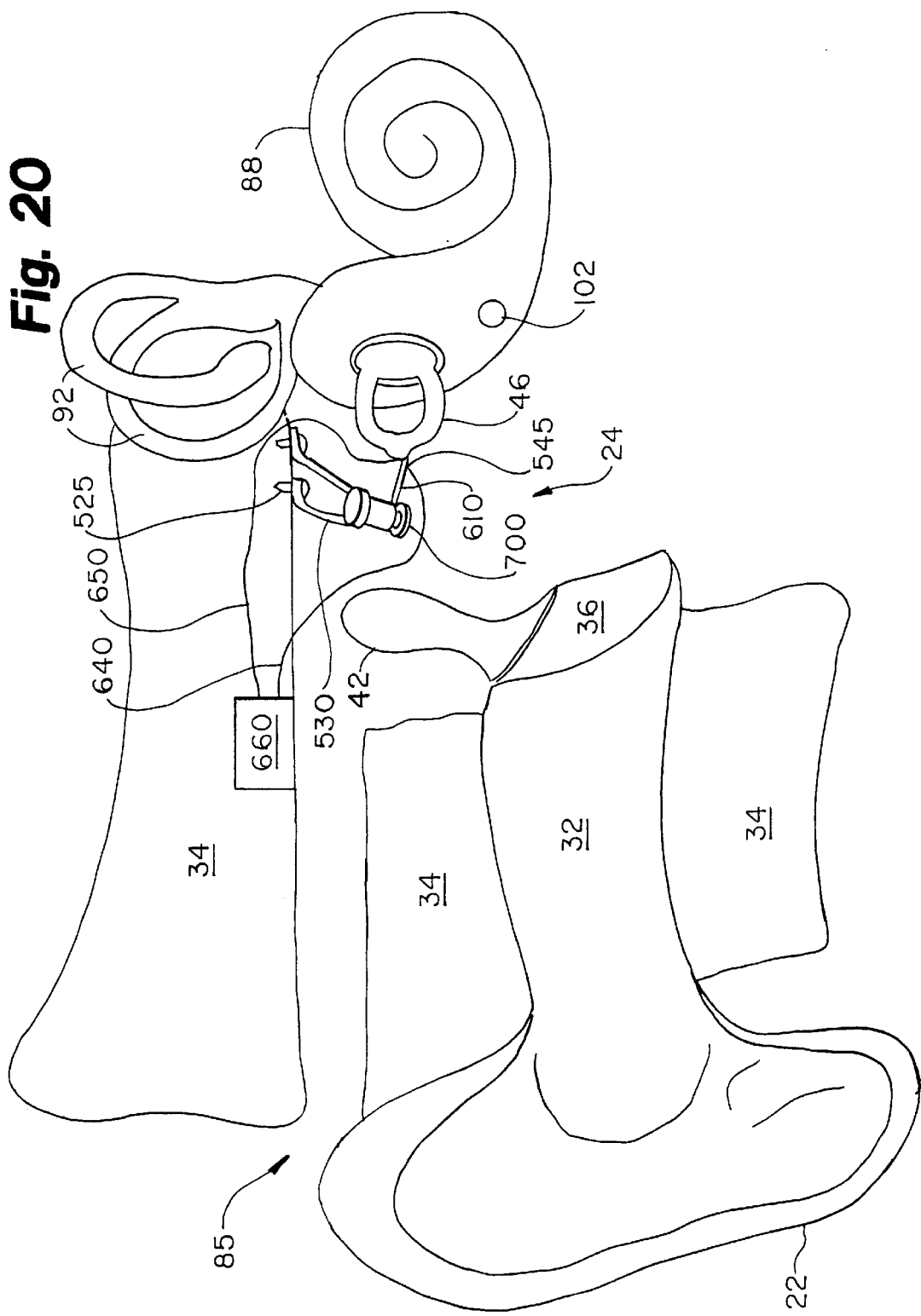
FIG. 20 is a view of an embodiment of the invention positioned in a human ear engaging a portion of the ossicular chain thereof.

Referring now to FIG. 20, electrical lead wires 640, 650 extend from transducer 545 and connect to electronics unit 660 at a separate location. Of course, a second transducer (not illustrated) may also be coupled to electronics unit 660 to facilitate receipt and delivery of information within the system to impart hearing to the patient.

Figure 27:
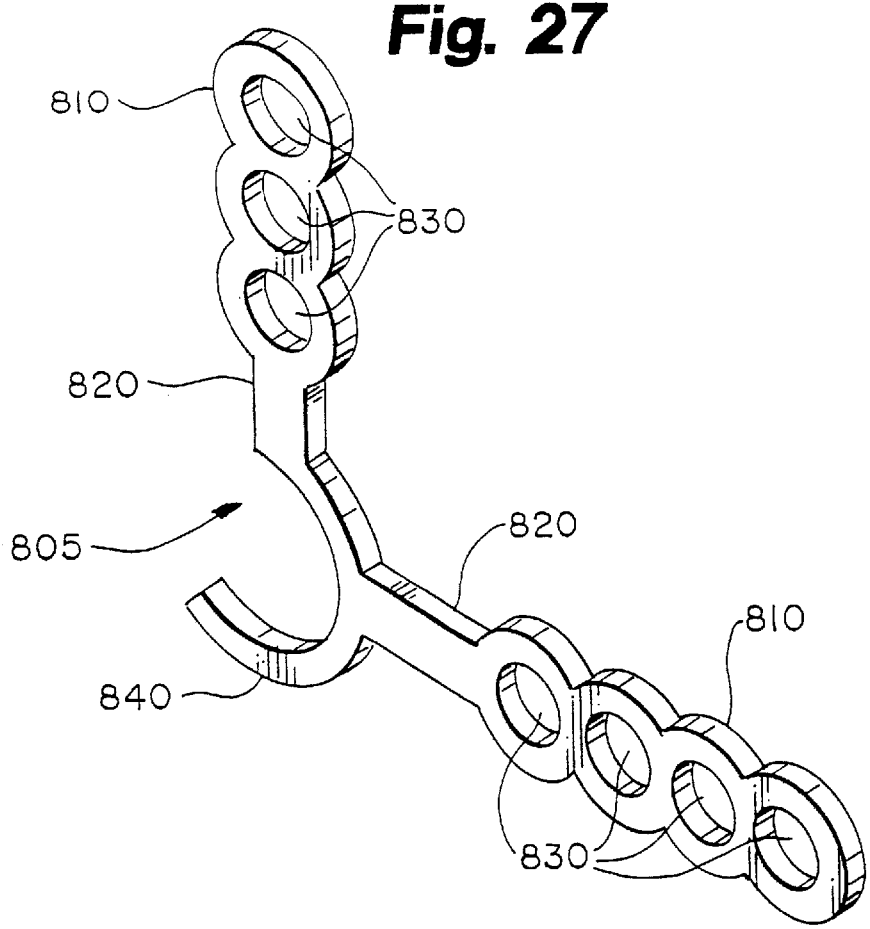
FIG. 27 is a perspective view of a further embodiment of the present invention.
Figure 28:
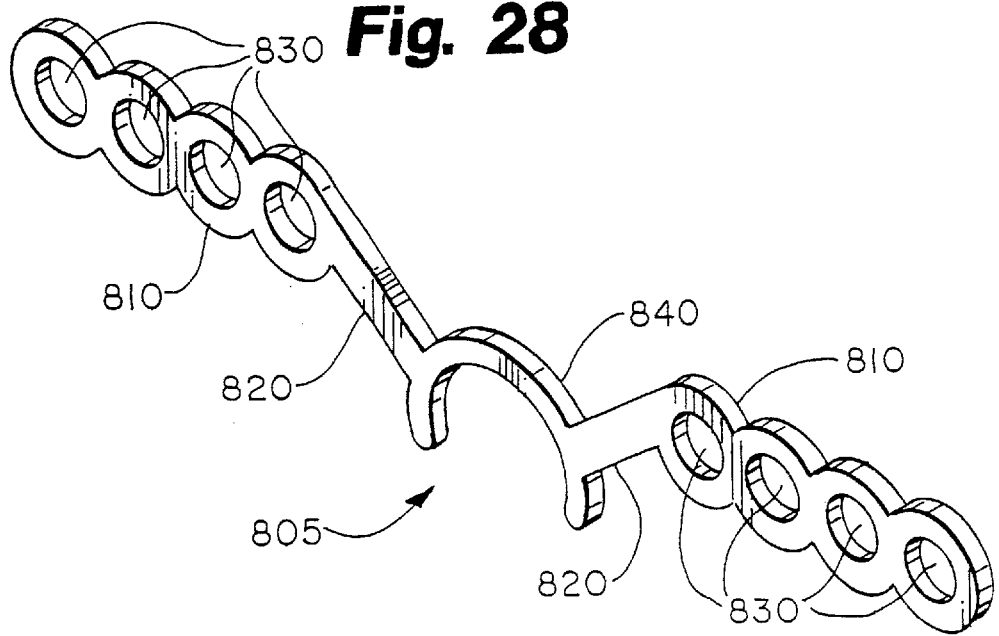
FIG. 28 is a perspective view of a further embodiment of the present invention.
Figure 29:
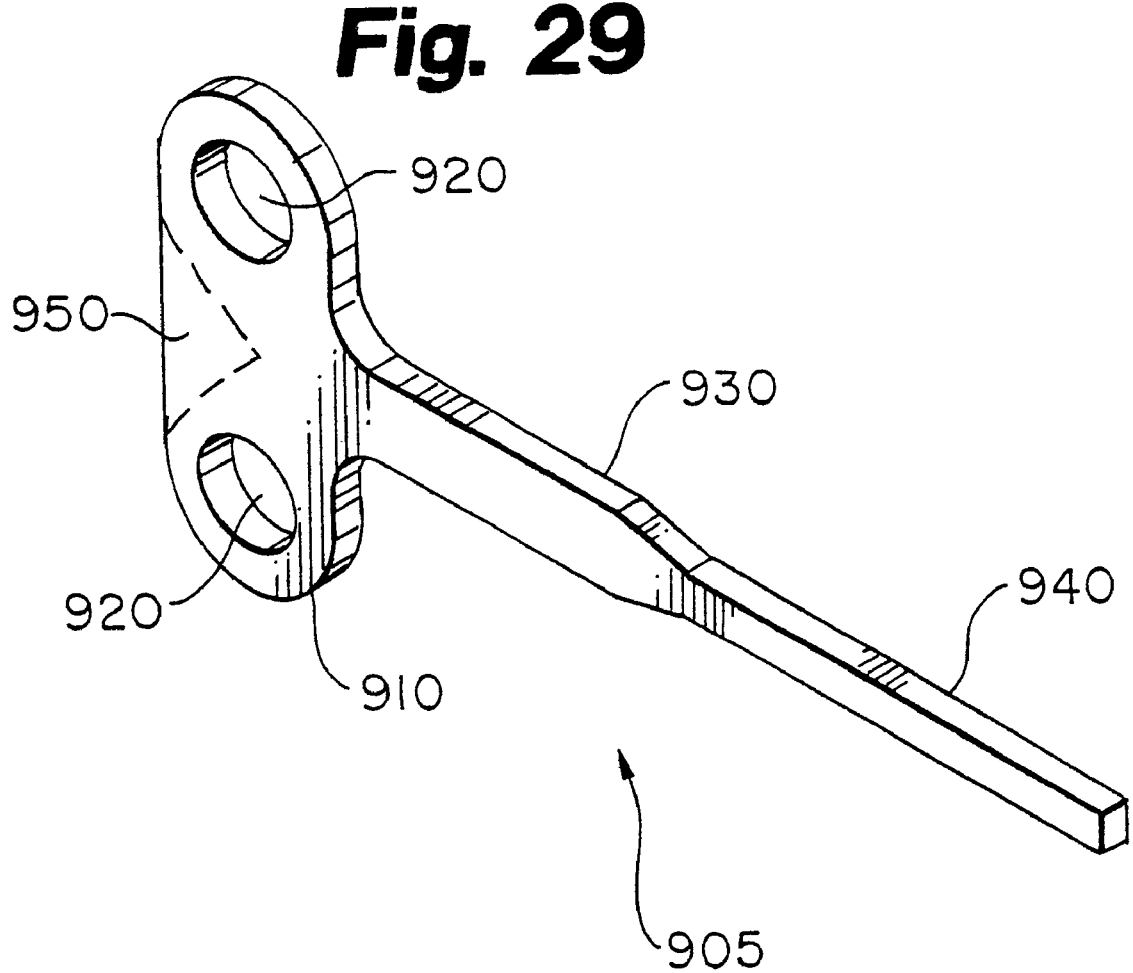
FIG. 29 is a perspective view of a further embodiment of the present invention.

In yet a further embodiment of the invention, as pictured in FIGS. 27–28, support assembly 805 is comprised of a pair of bendable, multiposition mounting tabes 810 by which support assembly 805 is mounted to mastoid 34, or other suitable bone. Mounting tabs 810 are characterized by multiple apertures 830 adapted for acceptance of a mechanical fastener. Depending from mounting tabs 810 are bendable frame members 820 which are commonly joined at collar 840. Mounting tabs 810 and members 820 may be deformed to aid in positioning a transducer within middle ear 24.

Collar 840 is constructed for receipt of a joint mechanism, such as joint 390 previously disclosed herein. Additional means extending from collar 840 may be utilized in unique circumstances to provide additional fastening capabilities. These additional means may optionally include apertures suitable for receiving fastening means; however, other structures are contemplated within the context of this invention.

In one embodiment of the invention, support system or assembly 905 is comprised of mounting plate 910, which is further characterized by two apertures 920. Depending from plate 910 is bendable primary member 930, of a predetermined width, which is connected to bendable secondary member 940 having a width smaller than primary member 930. Primary and secondary members 930, 940 comprise multiple width strengthening means for customized bending within a particular patient. Further, cut-out 950 may be optionally removed at mounting plate 910 to aid in mounting support assembly 905 to irregular surfaces. The remainder of the hearing assistance device (not pictured) is operatively coupled to primary and/or secondary members 930, 940.

Figure 26:
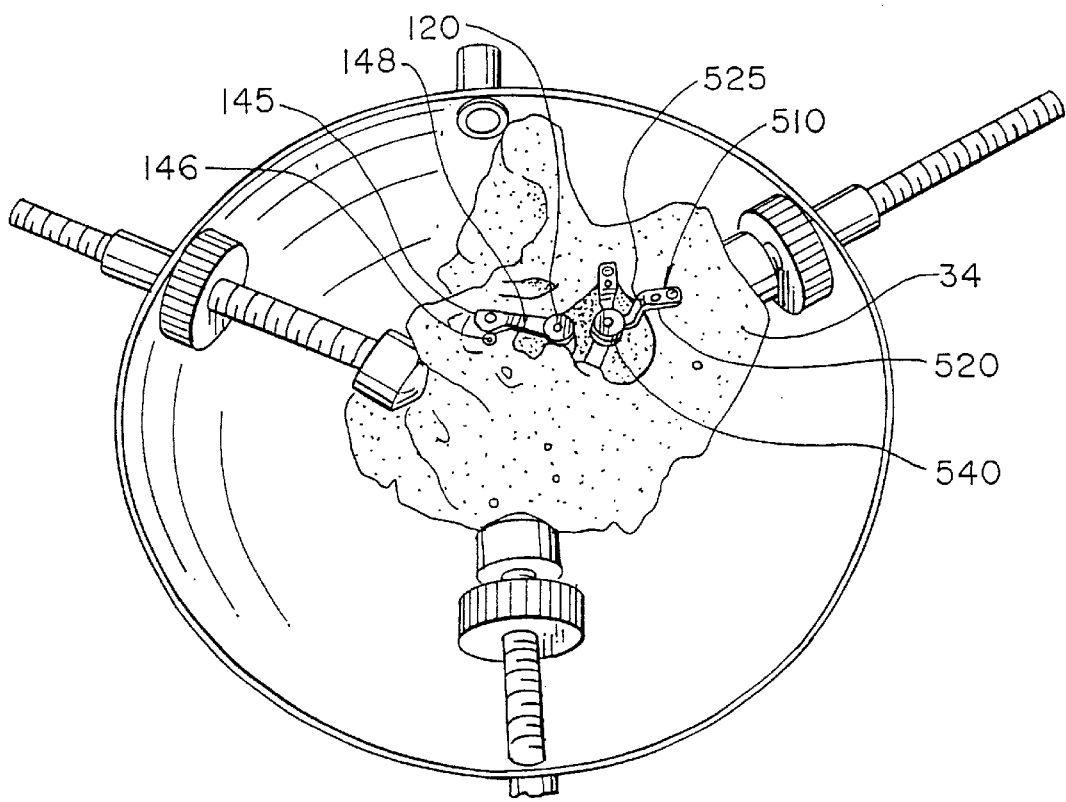
FIG. 26 is a view of two embodiments of the invention utilized as components of a hearing assistance system.

In the above-described embodiments, a variety of transducers are contemplated. The invention is useful in a partial middle ear implantation hearing aid system, and particular useful in a total middle ear implantation hearing aid system. In one such total middle ear implantation system, an input transducer is associated with stapes 46, transducing mechanical energy into an electrical signal which is amplified. It is further contemplated that the support assemblies, as described herein, may each also function as a component part of a larger system, such as a system wherein a second transducer is associated with malleus 42 and an embodiment of the invention as described herein is associated with stapes 46, the two transducers being coupled through an electronics unit. Refer to FIG. 26.

In one such embodiment, the system includes a programmer (not shown). The programmer includes an external (i.e., not implanted) programmer communicatively coupled to an external or implantable portion of the hearing assistance system, such as electronics unit 360. The programmer includes hand-held, desktop or a combination of hand-held and desktop embodiments for use by a surgeon or the patient in which the hearing assistance system is implanted.

In one embodiment, each of the programmer and the hearing assistance system includes an inductive element, such as coil, for inductively-coupled bi-directional transdermal communication between the programmer and the hearing assistance system. Inductive coupling is jus tone way to communicatively couple the programmer and the hearing assistance system, any other suitable technique of communicatively coupling the programmer and the hearing assistance system may also be used, including, but not limited to, radio-frequency (RF) coupling, infrared (IR) coupling, ultrasonic coupling, and acoustic coupling.

In one embodiment, the signals are encoded using pulse-code modulation (PCM), such as pulse-width telemetry or pulse-interval telemetry. In pulse-width telemetry, communication is by short bursts of a carrier frequency at fixed intervals, wherein the width of the burst indicates the presence of a "1" or a "0." In pulse-interval telemetry, communication is by short fixed-length bursts of a carrier frequency at variable time intervals, wherein the length of the time interval indicates the presence of a "1" or a "0." The data can also be encoded by any other suitable technique, including, but not limited to, amplitude modulation (AM), frequency modulation (FM), or other communication technique.

The data stream is formatted to indicate that data is being transmitted, where the data should be stored in memory (in the programmer or the hearing assistance system), and also includes the transmitted data itself. In one embodiment, for example, the data includes a wake-up identifier (e.g., 8 bits), followed by an address (e.g., 6 bits) indicating where the data should be stored in memory, followed by the data itself.

In a further embodiment, such communication includes programming of the hearing assistance system by a programmer (not shown) for adjusting hearing assistance parameters in the hearing assistance system to the programmer, such as for parameter verification or diagnostic purposes. Programmable parameters include, but are not limited to: on/off, standby mode, type of noise filtering for a particular sound environment, frequency response, volume, gain range, maximum power output, delivery of a test stimulus on command, and any other adjustable parameter. In one embodiment, certain ones of the programmable parameters (e.g., on/off, volume) are programmable by the patient, while others are of the programmable parameters (e.g., gain range, filter frequency responses, maximum power output, etc.) are programmable only by the physician.

Figure 30:
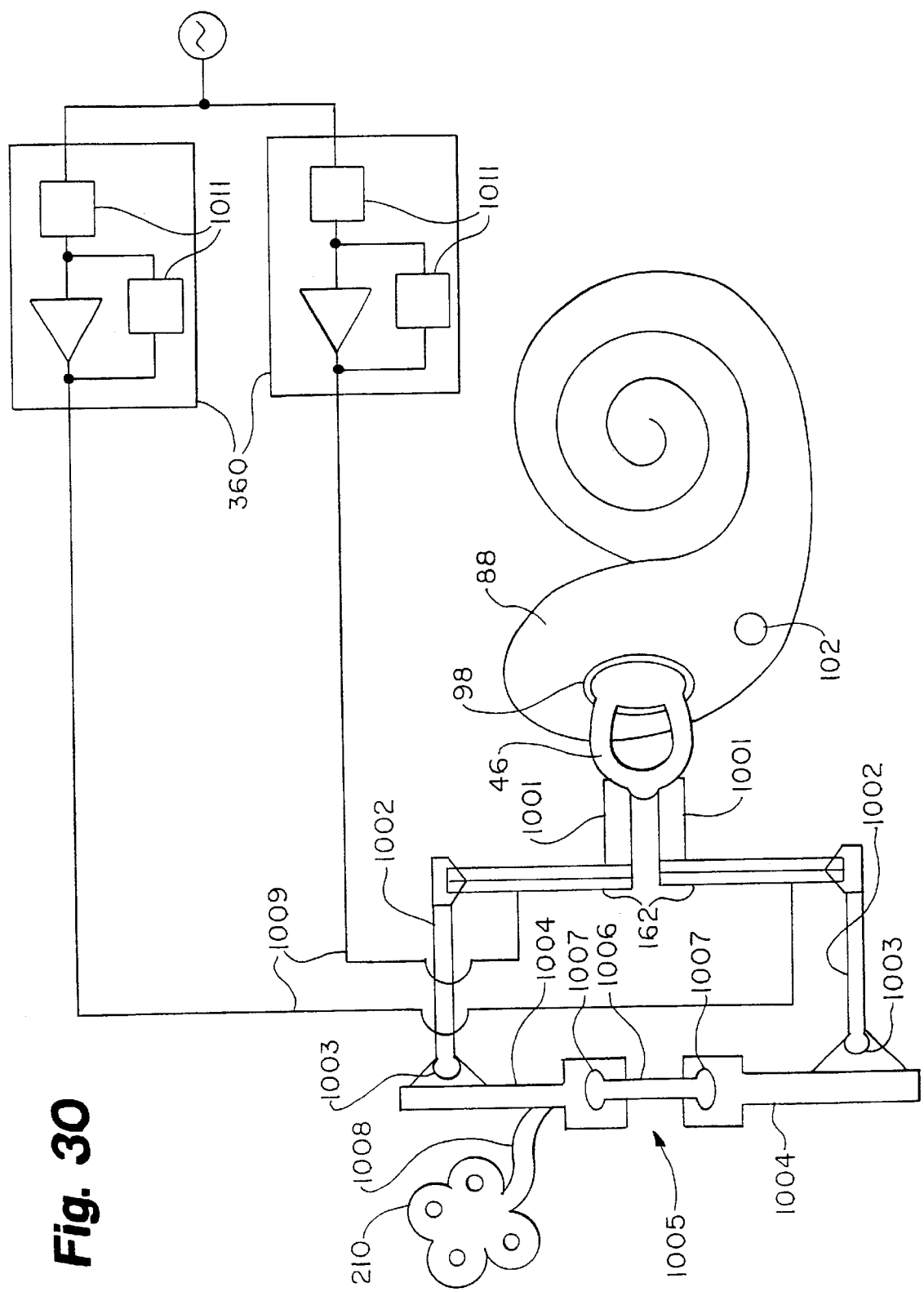
FIG. 30 shows a further embodiment of the present invention configured with dual transducers.

FIG. 30 shows an embodiment of the present invention configured with two transducers 162 that comprise adapters 1001 for fitting the transducers to an auditroy element such as the oval window or the stapes 46. The transducers are mounted on connectors 1002 and attached to mounting portions 1004 of support member 1005 by universal joints 1003. The mounting portions are fixably attached by connector 1006, which joins the mounting portions via ball-and-socket joints 1007. A bendable neck 1008 joins the support member to conformable mounting flange 210. Electrical leads 1009 electrically connect transducers 162 to the electronic unit 360, which is equipped with electrical signal processing elements 1011.

FIG. 31 shows another embodiment of the present invention that comprises dual transducers. The transducers 162 are in contact with different auditory elements such as the stapes 46 and the malleus 44. The transducers are mounted on mounting portions 1004 of support member 1005. A universal connector 1003 is employed to position one of the transducers. The support member is attached to conformable mounting flange 210 by bendable neck 1008.

The embodiments of FIGS. 30 and 31 exemplify mounting means. The transducers may be electromagnetic or employ piezoelectric materials. A transducer may be either an input transducer, an output transducer, or an input-output transducer. A bendable portion is not limited to the position shown, but may be used elsewhere; for instance, between the mounting portions or between a transducer and a mounting portion. The mounting means for the transducers may also use other means disclosed herein; for instance, a removably couplable hangers-and-sleeve means. The conformable mounting flange is also not limited to the illustrated embodiment; for instance, more than one may be used, one may have more mounting holes, be shaped as a rectangle, comprise an offset, or be attached with a pivotable means, or attached to another portion of the apparatus.

While the present invention has been described with reference to the preferred embodiments, the invention is not limited to the specific examples given. Various other modifications will occur to those of ordinary skill in the art, and other embodiments and modification can be made by those skilled in the art without departing from the spirit and scope of the invention as defined in the following claims.

What is claimed is:

1. A linkage apparatus for use in a hearing assistance system, the linkage apparatus comprising:
   a conformable mounting member configured for mounting on the internal bone structure of a patient, said mounting member defining at least one aperture to receive a bone screw member therethrough, and configured for coupling with a sleeve; and
   a sleeve, the sleeve selectably and removably couplable with a portion of the mounting member at a first end, to facilitate proper sizing and insertion of related hearing assistance system components into a patient's anatomy.

2. The apparatus of claim 1, further including a means for vibrating an anatomical structure inside an ear, said means operably attached to a second end of the sleeve.

3. The apparatus of claim 1, wherein a retaining means engages the first end of the sleeve, for holding the sleeve in position.

4. The apparatus of claim 1, wherein the vibrating means is a transducer assembly that includes a transducer.

5. The apparatus of claim 1, wherein the first end of the sleeve is further pivotally and rotatably couplable with the mounting member.

6. The apparatus of claim 1, wherein the sleeve defines a bore, and the transducer moves slidably within the bore of the sleeve.

7. The apparatus of claim 1, wherein the transducer is configured with a bendable portion, for facilitating positioning of the transducer against an anatomical structure inside the ear.

8. The apparatus of claim 1, wherein the mounting member comprises a conformable mounting flange, defining a plurality of bone screw holes, a flexible neck portion, and a hanger portion configured for coupling, the hanger portion being attached to the mounting flange by the neck.

9. The apparatus of claim 8, wherein a plurality of mounting flanges are connected by a plurality of necks to the hanger portion.

10. An implantable electromechanical linkage apparatus, for use in a system to improve the hearing of a hearing impaired subject, comprising:
    a conformable mounting flange configured for mounting on the internal bone structure of a patient, defining at least one bone screw hole, and including a coupling means; and
    a sleeve—defining a bore, rotatably, pivotably and selectably couplable, at a first end, to the mounting flange.

11. The apparatus of claim 10, wherein the mounting flange includes a hanger portion, defining a bore with integrated attachment means for a retaining nut, and including the coupling means within the bore.

12. The apparatus of claim 11, including a retaining nut, for securing the position of the sleeve while the sleeve is disposed within the hanger.

13. The apparatus of claim 12, wherein the hanger is attached to the mounting flange by a semi-rigid neck portion.

14. The apparatus of claim 10, wherein a transducer assembly, including a transducer means for vibrating an anatomical structure in the patients ear, engages the sleeve at a second end of the sleeve, such that a portion of the transducer assembly is slidable within the sleeve bore.

15. The apparatus of claim 12, wherein the retraining nut is designed to permit torquing sufficient to achieve retention of the nut in place while engaging and securing the first end of the sleeve, for a desired time period.

16. The apparatus of claim 11, wherein the hanger includes a sleeve receptacle opening that is positioned to allow removal of the sleeve and transducer assembly while the mounting flange is connected to bone.

17. The apparatus of claim 14, wherein the transducer assembly is a non-functional replica of the transducer assembly, and is made from a transparent material.

18. The apparatus of claim 17, where the non-functional replica of the transducer assembly is further made from a pliable material.

19. The apparatus of claim 16, wherein the first end of the sleeve, the coupling means of the hanger, and the sleeve receptacle opening of the hanger, are coated with a material having a coefficient of friction to facilitate the mounting, pivoting and rotating of the sleeve within the hanger.

20. The apparatus of claim 14, wherein the transducer is constructed from a material with piezoelectric properties.

21. The apparatus of claim 14, wherein the transducer assembly includes a selectable adjustable slide post member, with the transducer attached at a second end, the adjustable slide post being constructed from a shavable material, allowing the angling of the transducer.

22. The apparatus of claim 14, wherein the transducer assembly is coated with a material to promote the restraining of movement of the transducer assembly when the transducer assembly is at its most extended position in relation to the sleeve.

23. The apparatus of claim 14, wherein the transducer contains a bendable portion, to allow the angling of the distal end of the transducer.

24. The apparatus of claim 23, wherein the transducer depends from the transducer assembly at an angle of descent approximately 15° from a plane defined by a distal end of the transducer assembly.

25. The apparatus of claim 13, wherein a plurality of mounting brackets, each defining at least one bone screw hole, and a plurality of semi-rigid necks, each neck connecting a mounting bracket, are attached to the hanger portion.

26. An implantable electromechanical linkage apparatus, for use in a system to improve the hearing of a hearing impaired subject, being implantable within the middle ear after disarticulation of the ossicular chain, comprising:

a torquable retaining nut with external threading and defining a bore, with a spherical inner radius within the bore on a underside of the retaining nut, and slots, for screwing the retaining nut, on a top surface thereof; a flexible mounting flange, with a plurality of bone screw holes;

the hanger portion defining a bore, with a lubricated spherical inner radius within the bore on the underside of the hanger portion, a threaded portion within the bore for receiving the retraining nut, and a spherical receptacle opening in a side portion of the hanger;

a flexible neck portion connecting the mounting flange to the hanger;

a sleeve, defining a threaded bore, with a lubricated spherical shaped first end with a radius configured to pass through the spherical receptacle opening of the hanger, removably engaging the spherical radius within the bore of the hanger allowing the sleeve to pivot and rotate within the hanger bore, and a second end of the sleeve having a shape at the entry to the bore that is generally square, and the radius of the spherical first end of the sleeve matching the inner radius of the retaining nut, for securing the position of the sleeve; and a transducer assembly including a generally square adjustable slide post with a second end of the adjustable slide post being shavable for angling, a support element operably connected at a first surface to the second end of the adjustable slide post, a transducer portion, with piezoelectric properties, connected to a second surface of the support element by a flexible portion to allow further positioning of the transducer, and including operable electrical transducer connections, and a threaded spinner portion, movably connected to a first end of the adjustable slide post, with slots to facilitate screwing at a first end the spinner, the spinner being operable for screwing within the bore of the sleeve, drawing the adjustable slide post in or out of the bore of the sleeve, for positioning the transducer.

27. The apparatus of claim 26, wherein there are a plurality of mounting brackets and a plurality of flexible necks, each neck connecting a mounting bracket to the hanger portion.

28. The apparatus of claim 26, wherein the transducer has a flexible portion to allow angling of the transducer within the implantable area.

29. A method for mounting a transducer within the middle ear region, the method comprising:

bending a mounting flange to configure it for attachment to a bony structure within a middle ear region;

affixing the mounting flange to a bony structure within the middle ear;

selecting a sleeve from a plurality of sleeves, each of different lengths;

affixing a transducer assembly to a second end of the sleeve;

adjusting the overall length of the sleeve and attached transducer; and inserting a first end of the sleeve, with the attached transducer assembly, into a hanger, the hanger being attached to the mounting flange by a semi-rigid neck portion.

30. The method of claim 29, further comprising the steps of:

bending the semi-rigid neck portion to adjust alignment of the transducer with an auditory element in the ear.

31. The method of claim 29, further comprising the steps of:

removing the sleeve with attached transducer assembly;

adjusting the over-all length of the sleeve with attached transducer assembly for more generally aligning the transducer of the transducer assembly against the auditory element of the ear; and re-inserting the sleeve with attached transducer assembly into the hanger.

32. The method of claim 29, further comprising the steps of:

rotating and pivoting the sleeve, with attached transducer assembly, for finer alignment of the transducer against the auditory element of the ear; and fixing the transducer in position against the auditory element of the ear by tightening a restraining nut against the sleeve.

33. The method of claim 29, the method further comprising:

bending a transducer support, at a flexible portion of the transducer support, for finer alignment of the transducer against the auditory element of the ear.

34. The method of claim 29, wherein a model, made from a transparent and pliable material, is used in the first inserting step, in place of the operable transducer assembly, to assist in the alignment of the transducer against the auditory element of the ear.

35. A method for removing or replacing previously installed transducers, the method comprising:

loosening a sleeve restraining nut;

removing a first end of a sleeve, with an attached transducer assembly, from a fixed hanger;

selecting the sleeve from a plurality of sleeves, each of a different length;

affixing a transducer assembly to a second end of the sleeve;

adjusting the length of the sleeve and attached transducer;

shaving the adjustable slide post to angle the transducer;

re-inserting a first end of the sleeve with attached transducer assembly into the hanger to assess the position of a transducer attached to the transducer assembly, relative to its position with the target auditory element of the ear;

removing the sleeve with attached transducer assembly;

adjusting the length of the sleeve and attached transducer assembly for generally aligning a transducer of the transducer assembly against the auditory element of the ear;

re-inserting the sleeve and attached transducer assembly into the hanger;

rotating and pivoting the sleeve and attached transducer assembly for finer alignment of the transducer against the auditory element of the ear; and fixing the transducer in position against the auditory element of the ear by tightening the sleeve restraining nut against the sleeve.

36. The method of claim 35, wherein the shaving step is replaced by:

bending a transducer support, at a flexible portion of the transducer support at its proximal end, for finer alignment of the transducer against the auditory element of the ear.

37. The method of claim 35, wherein a model transducer assembly, made from a transparent material, is used in the affixing step, in place of the operable transducer assembly, to assist in the alignment of the transducer against the auditory element of the ear, and a further step, to be performed before the re-inserting step, comprising:

removing the model transducer assembly from the second end of the sleeve; and affixing a operable transducer assembly to the second end of the sleeve.

* * * * *